United States Patent
Wada et al.

(12)

(10) Patent No.: US 9,168,332 B2
(45) Date of Patent: Oct. 27, 2015

(54) HEMODIALYSIS APPARATUS, METHOD OF OPERATING HEMODIALYSIS APPARATUS, AND WATER CONTENT REMOVAL SYSTEM

(75) Inventors: Tomoyuki Wada, Tokyo (JP); Koji Shimoide, Tokyo (JP); Hiroshi Kurokawa, Tokyo (JP); Shingo Takesawa, Nobeoka (JP); Koichi Nakano, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 615 days.

(21) Appl. No.: 13/503,131

(22) PCT Filed: Oct. 22, 2010

(86) PCT No.: PCT/JP2010/068682
§ 371 (c)(1),
(2), (4) Date: Apr. 20, 2012

(87) PCT Pub. No.: WO2011/049196
PCT Pub. Date: Apr. 28, 2011

(65) Prior Publication Data
US 2012/0199533 A1    Aug. 9, 2012

(30) Foreign Application Priority Data

Oct. 23, 2009 (JP) .................................. 2009-244590
Mar. 8, 2010 (JP) .................................. 2010-050844
Mar. 29, 2010 (JP) .................................. 2010-075753

(51) Int. Cl.
*A61M 1/16* (2006.01)
*B01D 61/26* (2006.01)
(Continued)

(52) U.S. Cl.
CPC ................. *A61M 1/16* (2013.01); *A61M 1/165* (2014.02); *A61M 1/1641* (2014.02); *A61M 1/34* (2013.01);
(Continued)

(58) Field of Classification Search
USPC ........................... 210/142, 195.2, 646
See application file for complete search history.

(56) References Cited

U.S. PATENT DOCUMENTS

| 4,037,616 A | 7/1977 | Pinkerton |
| 4,178,240 A | 12/1979 | Pinkerton |

(Continued)

FOREIGN PATENT DOCUMENTS

| CN | 1658916 | 8/2005 |
| JP | 52-120593 | 10/1977 |

(Continued)

OTHER PUBLICATIONS

Search report from International Application No. PCT/JP2010/068682, mail date is Dec. 7, 2010.

(Continued)

*Primary Examiner* — Dirk Bass
(74) *Attorney, Agent, or Firm* — Greenblum & Bernstein, P.L.C.

(57) ABSTRACT

A hemodialysis apparatus includes a dialyzer, a quantitative vessel including a displaceable partition wall which partitions the inside of the quantitative vessel into a first chamber and a second chamber, a storage vessel which stores a dialysate, a dialysate exchange circuit which supplies the dialysate to the first chamber, and discharges a waste dialysate in the second chamber to the outside by the consequent displacement of the partition wall to the second chamber side, a dialysate supply circuit which supplies the dialysate in the first chamber to the dialyzer, and discharges the waste dialysate from the dialyzer to the second chamber by the displacement of the partition wall to the first chamber side, and a dialysate storage circuit which supplies the dialysate in the first chamber to the storage vessel by the displacement of the partition wall to the first chamber side.

12 Claims, 16 Drawing Sheets

(51) Int. Cl.
*B01D 61/32* (2006.01)
*B01D 61/28* (2006.01)
*A61M 1/34* (2006.01)

(52) U.S. Cl.
CPC ........... *A61M 1/3444* (2014.02); *A61M 1/3448* (2014.02); *A61M 1/342* (2013.01); *A61M 2205/128* (2013.01)

(56) References Cited

U.S. PATENT DOCUMENTS

| | | | |
|---|---|---|---|
| 4,197,196 | A | 4/1980 | Pinkerton |
| 4,209,391 | A | 6/1980 | Landau et al. |
| 4,267,040 | A | 5/1981 | Schal |
| 4,530,759 | A | 7/1985 | Schal |
| 4,770,769 | A | 9/1988 | Schael |
| 4,857,199 | A | 8/1989 | Cortial |
| 4,935,125 | A | 6/1990 | Era et al. |
| 5,871,694 | A | 2/1999 | Beden et al. |
| 6,042,784 | A | 3/2000 | Wamsiedler et al. |
| 2005/0020959 | A1* | 1/2005 | Brugger et al. ............. 604/4.01 |
| 2008/0202591 | A1 | 8/2008 | Grant et al. |
| 2009/0107902 | A1 | 4/2009 | Childers et al. |
| 2013/0118970 | A1 | 5/2013 | Beden et al. |

FOREIGN PATENT DOCUMENTS

| | | |
|---|---|---|
| JP | 55-073264 | 6/1980 |
| JP | 62-059592 | 12/1987 |
| JP | 64-062168 | 3/1989 |
| JP | 4-048061 | 8/1992 |
| JP | 5-31181 | 2/1993 |
| JP | 5-146505 | 6/1993 |
| JP | 5-146506 | 6/1993 |
| JP | 07-59848 | 3/1995 |
| JP | 8-10319 | 1/1996 |
| JP | 2000-126284 | 5/2000 |
| JP | 2001-153050 | 6/2001 |
| JP | 2003-284772 | 10/2003 |
| JP | 4395204 | 10/2009 |
| WO | 2008/106538 | 9/2008 |

OTHER PUBLICATIONS

Search report from International Preliminary Report on Patentability and Written Opinion for International Application No. PCT/JP2010/068682, mail date is May 24, 2012.
Taiwan Office action, mail date is Feb. 26, 2013.
Search report from E.P.O., mail date is Jan. 7, 2014.
Tokuma Nachi et al., "Physical Properties and Application to Lithium Batteries of Fluorinated Diethyl Carbonate", The 49th Battery Symosium in Japan, Nov. 5-7, 2008, in Sakai.
T. Kitagawa et al., "Application of highly oxidation-resistant fluoro-electrolyte to lithium-ion battery", The 49th Battery Symosium in Japan, Nov. 5-7, 2008, in Sakai.
Meiten Koh et al., "Properties of the electrolyte containing fluoroether", The 49th Battery Symosium in Japan, Nov. 5-7, 2008, in Sakai.
Foreign Japan Official Action dated Jul. 1, 2015.

* cited by examiner (A)            (B)

HEMODIALYSIS APPARATUS, METHOD OF OPERATING HEMODIALYSIS APPARATUS, AND WATER CONTENT REMOVAL SYSTEM

The present invention relates to a hemodialysis apparatus which dialyzes blood, a method of operating a hemodialysis apparatus, and a water content removal system for removing the water content from blood.

BACKGROUND ART

For instance, a hemodialysis apparatus includes a dialysis circuit which supplies and discharges a dialysate to and from a dialyzer. This dialysis circuit is provided with a quantitative vessel which houses a dialysate of a fixed quantity to be supplied to the dialyzer, and houses a waste dialysate of a fixed quantity that was discharged from the dialyzer. With a dialysis circuit, in a state where blood is caused to flow to a primary side of a dialysis membrane of the dialyzer, by discharging the dialysate from a secondary side of the dialyzer to the quantitative vessel while supplying the dialysate from the quantitative vessel to the secondary side of the dialysis membrane of the dialyzer, the dialysate is passed through the dialyzer, waste products contained in the blood are introduced into the dialysate, and the patient's blood is thereby subject to dialytic treatment (refer to Patent Document 1).

Moreover, in order to remove the excess water content contained in the patient's body, ultrafiltration treatment is performed in the foregoing dialytic treatment. In order to perform this ultrafiltration treatment, normally, an ultrafiltration line for removing the water content from the blood is connected to the waste fluid line that is more downstream than the dialyzer of the dialysis circuit. The ultrafiltration line is provided with, for instance, a pump, and the water content is sucked and removed from the blood inside the dialyzer by operating the pump (refer to Patent Document 1). Moreover, as another means for removing the water content from the blood, proposed is a method of providing a constant-pressure valve to a waste fluid line, maintaining a branch point of the waste fluid line and an ultrafiltration line to a positive pressure by the constant-pressure valve, and removing the water content of the blood in the dialysate through the ultrafiltration line (refer to Patent Document 2).

[Patent Document 1] Patent Publication JP-A-H5-146506
[Patent Document 2] Patent Publication JP-A-2000-126284

Meanwhile, in order to strictly management the amount of fluid contained in the patient's body, for instance, it is necessary to strictly control the fluid removal that is discharged from the ultrafiltration line. Thus, a quantitative pump is used as the pump of the ultrafiltration pump of foregoing Patent Document 1, and strictly controlled. Consequently, the control and the like of the hemodialysis apparatus become complicated and, for example, this causes the hemodialysis apparatus to become expensive. Moreover, with the constant-pressure valve of the dialysis circuit of foregoing Patent Document 2, not only does the control of the apparatus become difficult due to the control of the constant-pressure valve and the like, but also there is a possibility that the positive pressure at the branch point cannot be sufficiently maintained since the branch point of the waste fluid line and the ultrafiltration line is downstream of the dialyzer, and there may be cases where the fluid removal cannot be controlled with high precision.

SUMMARY

The present invention was devised in view of the foregoing points, and its object is to provide a hemodialysis apparatus, a method of operating such a hemodialysis apparatus, and a water content removal system which enable the fluid removal from blood to be controlled with high prevision based on easier control and mechanism.

In order to achieve the foregoing object, the present invention provides a hemodialysis apparatus comprising a dialyzer, a vessel including a displaceable partition wall which partitions the inside of the vessel into a first chamber and a second chamber, a storage vessel which stores a dialysate, a dialysate exchange circuit which supplies the dialysate to the first chamber and discharges a waste dialysate in the second chamber to the outside by the consequent displacement of the partition wall to the second chamber side, a dialysate supply circuit which supplies the dialysate in the first chamber to the dialyzer and discharges the waste dialysate from the dialyzer to the second chamber by the displacement of the partition wall to the first chamber side, and a dialysate storage circuit which supplies the dialysate in the first chamber to the storage vessel by the displacement of the partition wall to the first chamber side. Note that the expression "displacement" of the partition wall not only refers to the movement of the overall partition wall, and also includes cases where the partition wall itself becomes deformed and displaced.

According to the present invention, since a part of the dialysate in the first chamber can be supplied to the storage vessel by the displacement of the partition wall of the vessel, the water content of the blood corresponding to the amount of such dialysate can be discharged to the second chamber by utilizing the negative pressure of the second chamber that is consequently generated. Thus, fluid removal from blood can be controlled with high precision based on easier control and mechanism.

The vessel may also include a resilience application device which applies resilience to the partition wall for returning to the first chamber side when the partition wall is displaced to the second chamber side. In the foregoing case, since the displacement of the partition wall of the vessel can be performed based on resilience, for instance, a drive source that is needed for power feeding is not required, and the configuration and control of the apparatus can be simplified.

The storage vessel may include a displaceable partition wall which partitions the inside of the storage vessel into two storage chambers, and the dialysate storage circuit may be configured to be capable of selectively supplying the dialysate in the first chamber to the respective storage chambers of the storage vessel, and of selectively discharging the dialysate in each of the storage chambers. In the foregoing case, since the dialysate can be alternately supplied to the two storage chambers of the storage vessel and, while supplying the dialysate to one storage chamber, the dialysate in the other storage chamber can be discharged, the dialysate can be continuously supplied to the storage vessel. Thus, ultrafiltration from the blood can be performed continuously, and ultrafiltration can be performed efficiently.

The dialysate storage circuit may be configured to be capable of discharging the dialysate in each of the storage chambers to the dialysate exchange circuit. In the foregoing case, the circuit for discharging the dialysate in the storage vessel can be simplified.

The foregoing hemodialysis apparatus further includes a control unit which implements a first step of supplying the dialysate to the first chamber of the vessel through the dialysate exchange circuit, displacing the partition wall of the vessel to the second chamber side, and discharging the waste dialysate in the second chamber of the vessel through the dialysate exchange circuit; a second step of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side; and a third step of supplying the dialysate in the first chamber to the dialyzer through the dialysate supply circuit and discharging the waste dialysate from the dialyzer to the second chamber by the displacement of the partition wall to the first chamber side, and the control unit alternately implements at least either the second step or the third step, and the first step. Note that only one of either the second step or the third step may be implemented, or the second step and the third step may be implemented intermittently, continuously or simultaneously. Moreover, the order thereof may be such that the third step is implemented first.

Moreover, with the foregoing hemodialysis apparatus, the vessel, the storage vessel, at least a part of the dialysate exchange circuit, at least a part of the dialysate supply circuit, and at least a part of the dialysate storage circuit may be formed on a cassette unit which can be freely attached to and detached from the hemodialysis apparatus. In the foregoing case, the cassette unit formed with the vessel, the storage vessel and the like can be removed from the apparatus, and the maintenance of the hemodialysis apparatus can be performed by replacing that cassette unit with a new cassette unit. Consequently, even a person without any professional knowledge, skill or experience can perform the maintenance easily, and the quality of maintenance can also be ensured. Thus, the patient can perform ongoing hemodialysis treatment by using the hemodialysis apparatus even at home or in a depopulated area and, for instance, the patient's QOL (Quality of Life) can be improved.

The foregoing hemodialysis apparatus may further include a blood removal-side circuit which supplies blood of a living subject to the dialyzer, and a retransfusion-side circuit which returns the blood in the dialyzer to the living subject, and at least a part of the blood removal-side circuit and at least a part of the retransfusion-side circuit may be formed on a cassette unit which can be freely attached to and detached from the hemodialysis apparatus.

In addition, in a valve for supplying and discharging the fluid to and from the vessel and the storage vessel, a portion that comes into contact with the fluid may be formed on the cassette unit and a portion that does not come into contact with the fluid may be formed on a body of the hemodialysis apparatus. In the foregoing case, upon replacing the cassette unit, the portion that does not come into contact with the fluid and will not become contaminated or deteriorated easily can be left on the body of the apparatus, and the portion that comes into contact with the fluid and will become contaminated or deteriorated easily can be replaced. Thus, it is possible to replace only the portion that has a substantial need for maintenance, and the maintenance cost of the hemodialysis apparatus can be reduced.

From a different perspective, the present invention provides a method of operating a hemodialysis apparatus, the hemodialysis apparatus including a dialyzer, a vessel including a displaceable partition wall which partitions the inside of the vessel into a first chamber and a second chamber, a storage vessel which stores a dialysate, a dialysate exchange circuit which supplies the dialysate to the first chamber and discharges a waste dialysate in the second chamber to the outside by the consequent displacement of the partition wall to the second chamber side, a dialysate supply circuit which supplies the dialysate in the first chamber to the dialyzer and discharges the waste dialysate from the dialyzer to the second chamber by the displacement of the partition wall to the first chamber side, and a dialysate storage circuit which supplies the dialysate in the first chamber to the storage vessel by the displacement of the partition wall to the first chamber side, wherein the method includes a step of causing a control unit to implement a first step of supplying the dialysate to the first chamber of the vessel through the dialysate exchange circuit, displacing the partition wall of the vessel to the second chamber side, and discharging the waste dialysate in the second chamber of the vessel through the dialysate exchange circuit; a second step of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side; and a third step of supplying the dialysate in the first chamber to the dialyzer through the dialysate supply circuit and discharging the waste dialysate from the dialyzer to the second chamber through the dialysate supply circuit by the displacement of the partition wall to the first chamber side, and a step of causing the control unit to alternately implement at least either the second step or the third step, and the first step. Note that only one of either the second step or the third step may be implemented, or the second step and the third step may be implemented intermittently, continuously or simultaneously. Moreover, the order thereof may be such that the third step is implemented first.

Moreover, from yet a different perspective, the present invention provides a water content removal system for removing water content from blood, comprising a separator through which blood passes and which separates the water content from the blood, a vessel including a displaceable partition wall which partitions the inside of the vessel into a first chamber and a second chamber, a storage vessel which stores a predetermined fluid, a first circuit which supplies the fluid to the first chamber of the vessel, a second circuit which discharges the water content in the second chamber of the vessel, a third circuit which supplies the fluid in the first chamber of the vessel to the storage vessel, and a fourth circuit which discharges the water content from the separator to the second chamber, wherein the vessel is configured to be capable of displacing the partition wall to the first chamber side to push out the fluid from the first chamber and store the fluid in the storage vessel through the third circuit, and of discharging the water content from the separator to the second chamber through the fourth circuit by utilizing a negative pressure of the second chamber that has been generated by the displacement of the partition wall to the first chamber side.

According to the present invention, it is possible to supply a predetermined fluid in the first chamber to the storage vessel based on the displacement of the partition wall of the vessel, and cause the water content of the blood corresponding to the amount of such fluid to become separated from the separator and flow into the second chamber by utilizing the negative pressure of the second chamber that is consequently generated. Thus, an amount of water content removal from blood can be controlled with high precision based on easier control and mechanism.

According to the present invention, since the amount of water content removal from blood can be controlled with high precision based on easier control and mechanism, it is possible, for instance, to realize an inexpensive hemodialysis apparatus and a water content removal system. Moreover, it is also possible to achieve the downsizing of the apparatus and the reduction of power consumption. In addition, since a pump for water content removal is not required, it is possible to eliminate the maintenance of such a pump. It is also possible to reduce troubles related to the pump. Moreover, since components related to the pump can be reduced in the least, it is possible to reduce the malfunction risk and additionally reduce noise.

DETAILED DESCRIPTION

Figure 1:
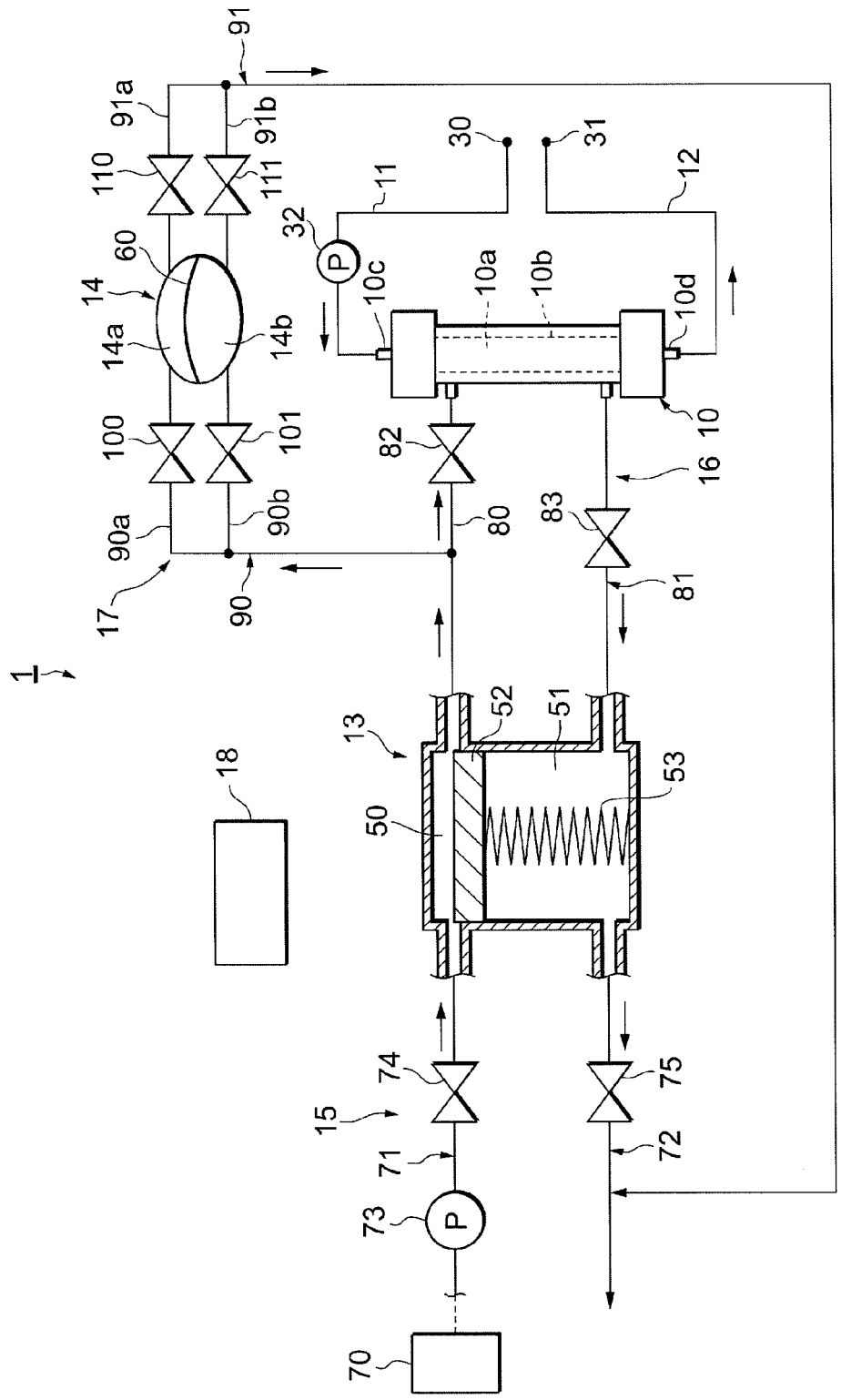
FIG. 1 is a schematic diagram showing an outline of the configuration of the hemodialysis apparatus.

The preferred embodiments of the present invention are now explained with reference to the drawings. FIG. 1 is an explanatory diagram showing an outline of the configuration of a hemodialysis apparatus 1 according to this embodiment.

The hemodialysis apparatus 1 includes, for example, a dialyzer 10, a blood removal-side circuit 11, a retransfusion-side circuit 12, a quantitative vessel 13, a storage vessel 14, a dialysate exchange circuit 15, a dialysate supply circuit 16, a dialysate storage circuit 17, and a control unit 18.

The dialyzer 10 is, for example, a hollow fiber module with a hollow fiber membrane built therein, and can pass a dialysate through a secondary side 10b while passing the patient's blood through a primary side 10a, and cause waste products as unwanted components of the blood on the primary side 10a to permeate to the secondary side 10b through a membrane, and thereby dialyze the blood. Moreover, the dialyzer 10 can separate the water content of blood from the blood on the primary side 10a to the secondary side 10b through the membrane. Note that the foregoing water content includes at least the water contained in the blood, and may also contain micro substances such as ions and waste products contained in the blood that pass through the membrane.

The blood removal-side circuit 11 is connected, for example, from a needle part 30 that is inserted into the patient to an inlet end 10c on the primary side 10a of the dialyzer 10. The retransfusion-side circuit 12 is connected from an outlet end 10d on the primary side 10a of the dialyzer 10 to another needle part 31. The blood removal-side circuit 11 is provided with a pump 32.

The quantitative vessel 13 is formed, for example, in a cylindrical shape, and includes, for instance, a displaceable partition wall 52 which partitions an inner space having a constant volume into a first chamber 50 and a second chamber 51 in an axial direction, and a spring 53 as a resilience application device which applies resilience to the partition wall 52 for returning to the first chamber 50 side while allowing the displacement of the partition wall 52. Thus, the quantitative vessel 13 includes a self return-type partition wall 52.

The partition wall 52 is formed, for example, in a piston shape which moves in the axial direction. When the partition wall 52 moves to the first chamber 50 side and the volume of the first chamber 50 decreases, the volume of the second chamber 51 increases by that much. When the partition wall 52 moves to the second chamber 51 side and the volume of the second chamber 51 decreases, the volume of the first chamber 50 increases by that much. The spring 53 is provided, for example, to the second chamber 51 side of the partition wall 52, connected to a bottom face of the second chamber 51 and a lower face of the partition wall 52, and generates resilience to the first chamber 50 side when the partition wall 52 moves to the second chamber 51 side.

Note that when there is only one system configured from the vessel 13, the dialysate exchange circuit 15 and the dialysate supply circuit 16 as shown in the drawings, the supply of the dialysate to the dialyzer 10 will be intermittent. In order to prevent this, two same systems may be installed and these may be connected to the dialyzer 10 in parallel. In these two systems, with the vessel 13 of one system and the vessel 13' of the other system, by controlling the valves so that the replenishment of a new dialysate in the vessel 13 and the discharge of the waste dialysate from the vessel 13, and the supply of a new dialysate from the vessel 13' to the dialyzer 10 and the supply of the waste dialysate from the dialyzer 10 to the vessel 13' are performed alternately, the hemodialysis can be performed without any pause, and, for example, it is possible to shorten the dialyzing time and alleviate the burden on the dialytic patient.

The storage vessel 14 includes a displaceable partition wall 60 which partitions an inner space of a constant volume into a first storage chamber 14a and a second storage chamber 14b, and can store a dialysate as the predetermined fluid in the respective storage chambers 14a, 14b. The partition wall 60 is configured, for example, from a rubber diaphragm or the like. With the first storage chamber 14a and the second storage chamber 14b, the partition wall 60 is displaced based on an internal pressure and changes the volume, and, when the volume of one chamber increases, the volume of the other chamber decreases by that much. The partition wall 60 is provided at the center inside the storage vessel 14, and the maximum volume of the second storage chamber 14b when the partition wall 60 moves maximally to the first storage chamber 14a side and the maximum volume of the first storage chamber 14a when the partition wall 60 moves maximally to the second storage chamber 14b side are the same.

Moreover, the maximum volume of the first storage chamber 14a and the second storage chamber 14b is smaller than the maximum volume of the first chamber 50 of the quantitative vessel 13.

The dialysate exchange circuit 15 includes, for example, a first circuit 71 that leads from the dialysate supply source 70 to the first chamber 50 of the quantitative vessel 13, and a second circuit 72 that leads from the second chamber 51 of the quantitative vessel 13 to the outside of the apparatus. The first circuit 71 is provided with a pump 73 for pressure-feeding the dialysate of the dialysate supply source 70 to the first chamber 50, and an on-off valve 74 for opening and closing the circuit 71. The second circuit 72 is provided with an on-off valve 75 for opening and closing the circuit 72.

The dialysate supply circuit 16 includes, for example, a third circuit 80 that leads from the first chamber 50 of the quantitative vessel 13 to the secondary side 10b of the dialyzer 10, and a fourth circuit 81 that leads from the secondary side 10b of the dialyzer 10 to the second chamber 51 of the quantitative vessel 13. The third circuit 80 and the fourth circuit 81 are respectively provided with on-off valves 82, 83.

The dialysate storage circuit 17 includes, for example, a fifth circuit 90 that leads to the first chamber 50 of the quantitative vessel 13 and the respective storage chambers 14a, 14b of the storage vessel 14, and a sixth circuit 91 that leads to the respective storage chambers 14a, 14b of the storage vessel 14 and the second circuit 72.

Guiding branches 90a, 90b that lead to the storage chambers 14a, 14b are formed on the fifth circuit 90, and the guiding branches 90a, 90b are provided with on-off valves 100, 101 as switching devices for selectively supplying the dialysate from the first chamber 50 of the quantitative vessel 13 to the two storage chambers 14a, 14b.

Guiding branches 91a, 91b that lead to the storage chambers 14a, 14b are formed on the sixth circuit 91, and the guiding branches 91a, 91b are provided with on-off valves 110, 111 as switching devices for selectively discharging the dialysate from the two storage chambers 14a, 14b.

Note that, in this embodiment, the upstream part of the third circuit 80 and the fifth circuit 90 is a common circuit, and is branched midway.

The control unit 18 controls the operation of, for example, the dialysate supply source 70, the pumps 32, 73, and the on-off valves 74, 75, 82, 83, 100, 101, 110, 111. The control unit 18 is, for example, a computer, and can implement the method of operating the hemodialysis apparatus 1 described later by executing a predetermined program stored in a memory.

The method of operating the hemodialysis apparatus 1 configured as described above is now explained. During hemodialysis treatment, the needle parts 30, 31 are inserted into the patient, and the patient's blood is supplied to the dialyzer 10 through the blood removal-side circuit 11. The blood passes through the primary side 10a of the dialyzer 10, and is thereafter returned to the patient through the retransfusion-side circuit 12.

Figure 2:
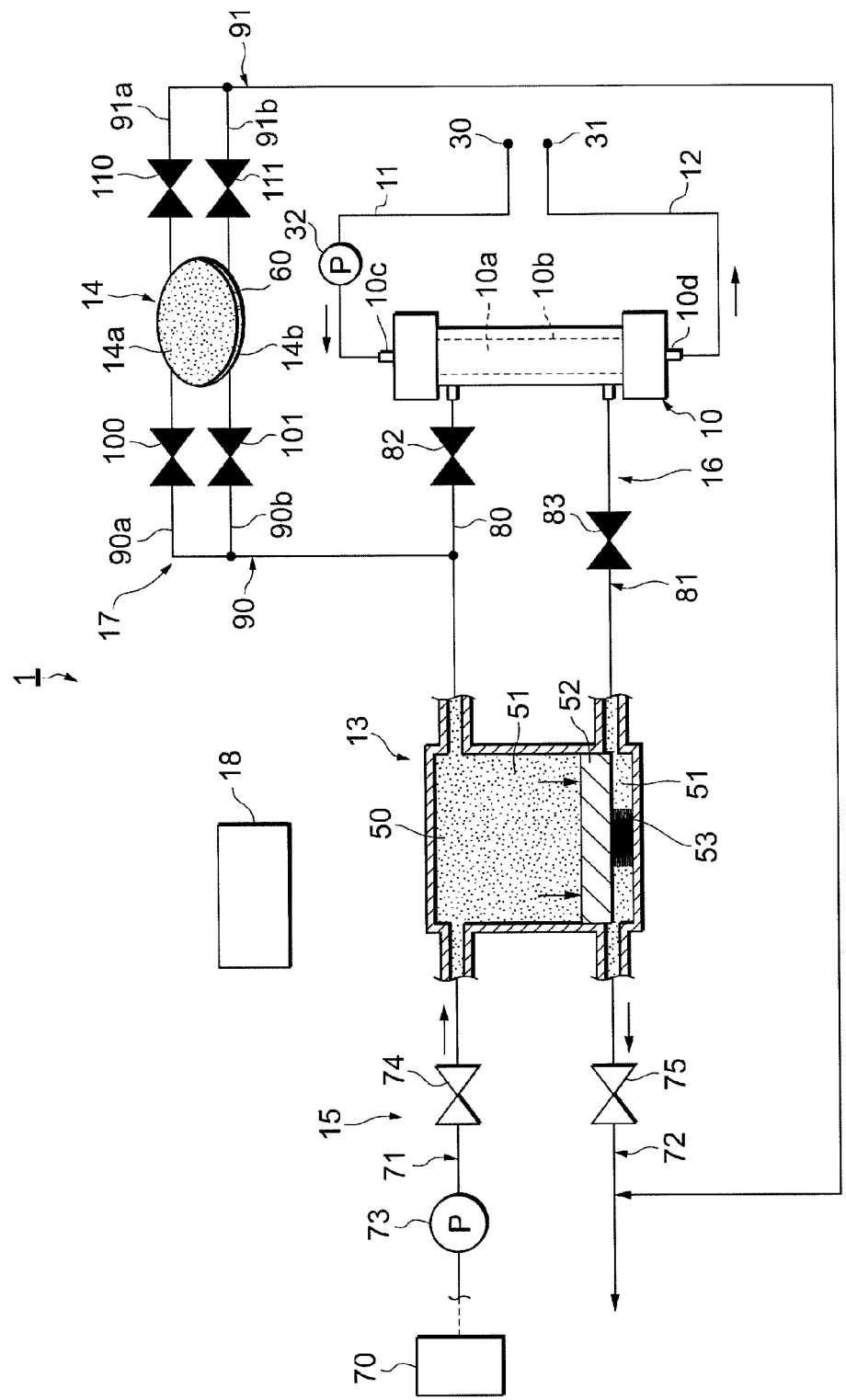
FIG. 2 is an explanatory diagram showing the state of the hemodialysis apparatus in the first step.

Meanwhile, on the supplying side of the dialysate, for example, as shown in FIG. 2, the on-off valves 100, 101, 110, 111, 82, 83 are closed, the on-off valves 74, 75 are opened, and a new dialysate of the dialysate supply source 70 is supplied into the first chamber 50 of the quantitative vessel 13 by the pump 73. Consequently, the new dialysate is filled in the first chamber 50, the partition wall 52 is pushed toward the second chamber 51 against the resilience of the spring 53, and the volume of the first chamber 50 thereby increases. Pursuant to the above, the volume of the second chamber 51 decreases, and the waste dialysate (dialysate that passed through the dialyzer 10) that was previously filled in the second chamber 51 is pushed out by the partition wall 52, and discharged outside through the second circuit 72 (first step). Note that, in the foregoing case, a dialysate is filled in advance, for instance, in the first storage chamber 14a of the storage vessel 14.

Figure 3:
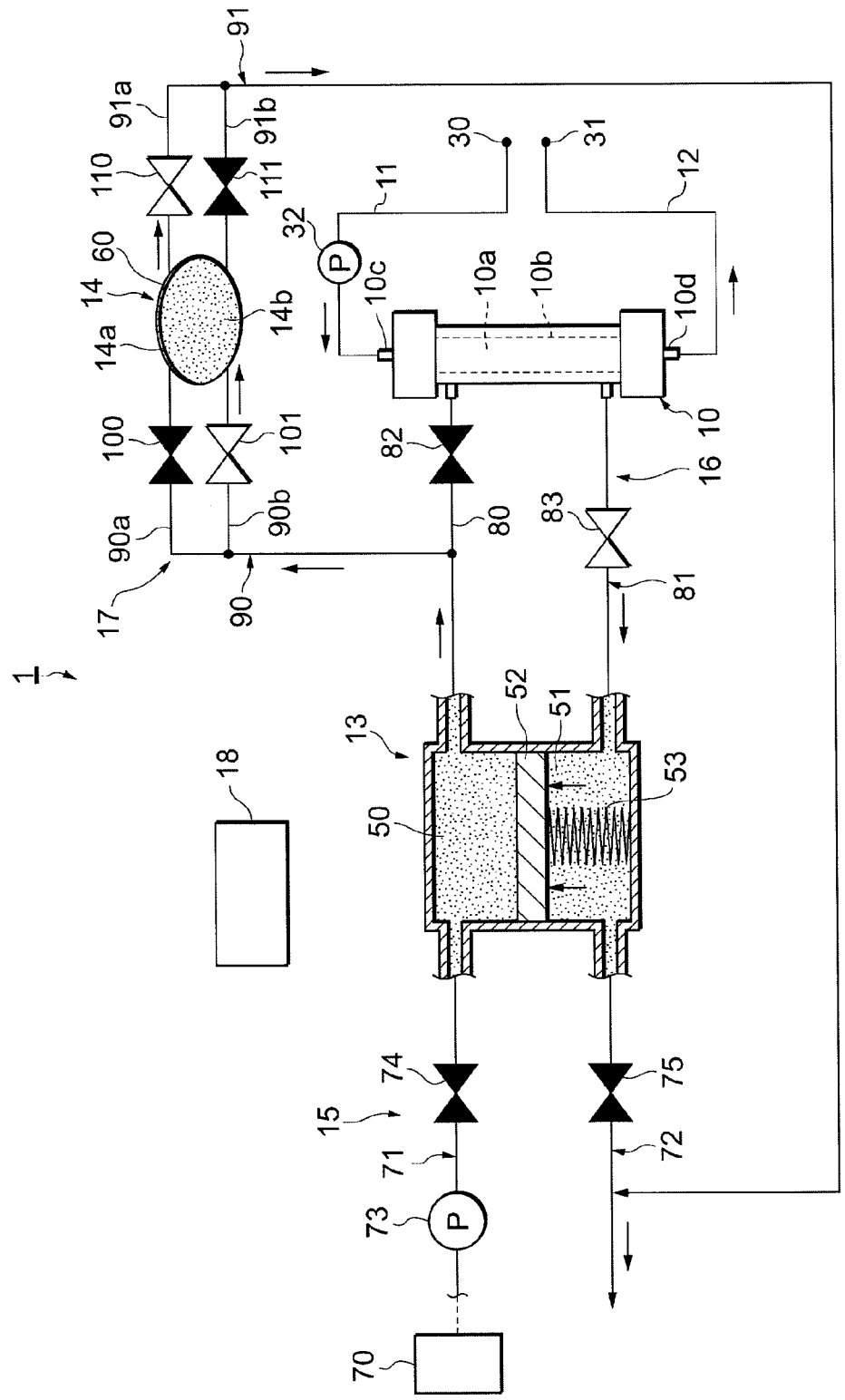
FIG. 3 is an explanatory diagram showing the state of the hemodialysis apparatus in the second step.

Subsequently, for example, as shown in FIG. 3, the on-off valves 74, 75 are closed, the on-off valves 101, 110, 83 are opened, and the partition wall 52 moves to the first chamber 50 side based on the resilience of the spring 53 of the quantitative vessel 13. Consequently, the dialysate of a fixed quantity in the first chamber 50 is pushed out and such dialysate is supplied to the second storage chamber 14b of the storage vessel 14 through the fifth circuit 90 (first case). Moreover, since the on-off valve 74 is closed, the second chamber 51 is depressurized due to the movement of the partition wall 52 and becomes a negative pressure, the water content in the blood on the primary side 10a of the dialyzer 10 flows to the secondary side 10b based on the negative pressure, and the water content is discharged to the second chamber 51 through the fourth circuit 81. A predetermined amount of water content is thereby removed from the blood (second step). The fluid removal in the foregoing case is an amount equal to the volume that increased in the second chamber 51 based on the movement of the partition wall 52 of the quantitative vessel 13, and this is the same as the amount equal to the amount that decreased in the first chamber 50; that is, the same as the amount of dialysate that was supplied to the second storage chamber 14b of the storage vessel 14 (amount equal to the maximum volume of the second storage chamber 14b).

With the storage vessel 14, when the dialysate is supplied to the second storage chamber 14b, the partition wall 60 moves to the first storage chamber 14a side, and the dialysate that was consequently pushed out is discharged outside through the sixth circuit 91 and the second circuit 72. Note that, if the circuit 91 through which the pushed-out dialysate flows takes on a configuration of being connected to the fluid channel 11 or 12 on the blood circuit side, the dialysate that is discharged from the storage vessel 14 will function as a replenisher to the patient. In the foregoing case, since the amount of dialysate that is discharged from the storage vessel 14 and the amount that is subject to ultrafiltration will coincide, it is guaranteed that the replenisher amount and the fluid volume subject to ultrafiltration will be balanced (On-line HDF).

Figure 4:
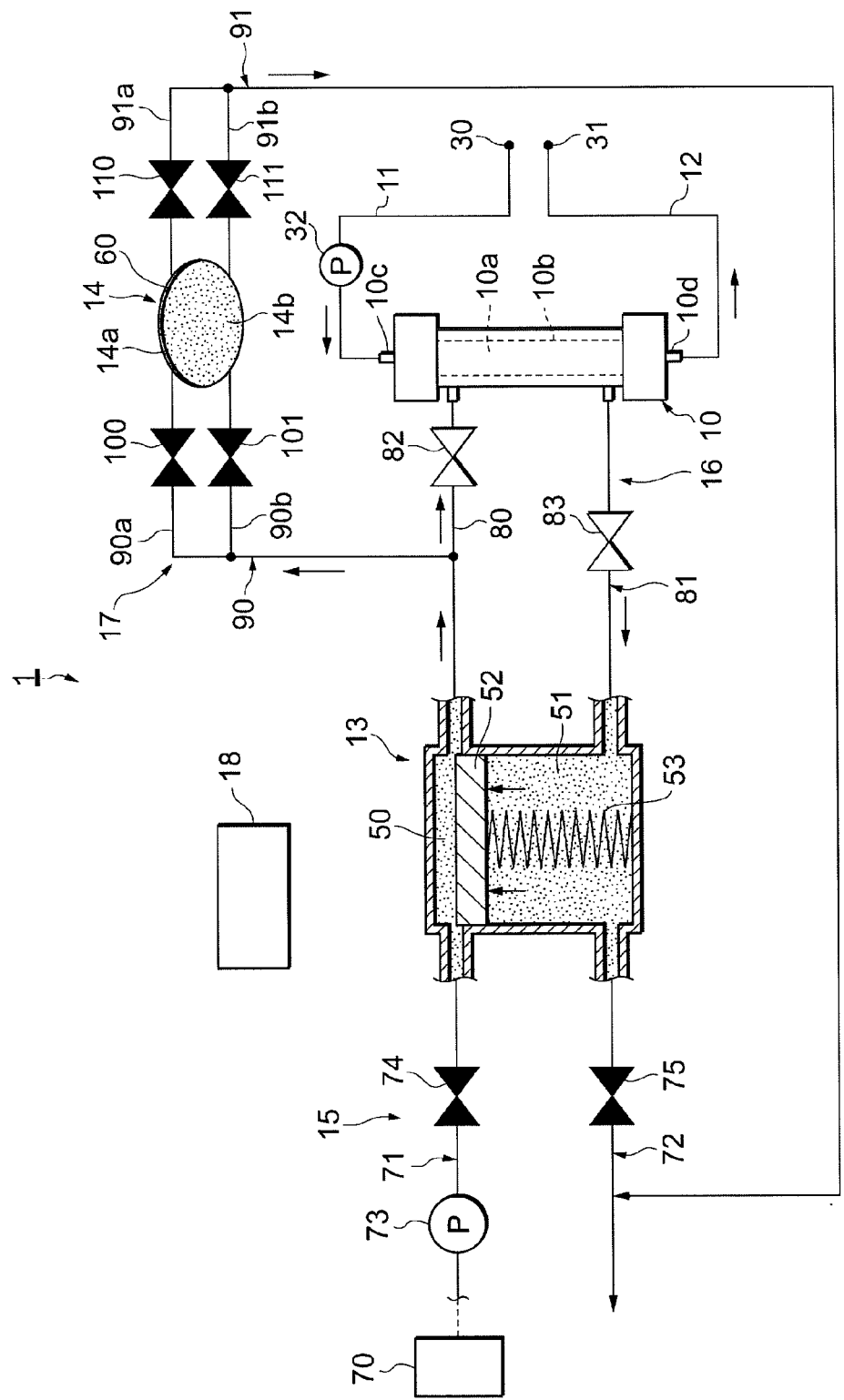
FIG. 4 is an explanatory diagram showing the state of the hemodialysis apparatus in the third step.

When the second storage chamber 14b is filled with the dialysate and the water content of the blood flows into the second chamber 51, subsequently, as shown in FIG. 4, the on-off valves 101, 110 are closed and the on-off valve 82 is opened. When the partition wall 52 of the quantitative vessel 13 moves further toward the first chamber 50 side due to the resilience of the spring 53, the remainder of the dialysate in the first chamber 50 is supplied to the secondary side 10b of the dialyzer 10 through the third circuit 80. On the secondary side 10b of the dialyzer 10, the waste products that passed through the membrane from the patient's bloods on the primary side 10a are taken in the dialysate. Subsequently, the waste dialysate that passed through the dialyzer 10 flows into the second chamber 51 of the quantitative vessel 13 through the fourth circuit 81 (third step). Here, since the volume of the second chamber 51 increases in the amount that the volume of the first chamber 50 decreases due to the movement of the partition wall 52, the dialysate that is pushed out from the first chamber 50 to the dialyzer 10 side and the amount of waste dialysate that is introduced into the second chamber 51 will coincide.

Figure 5:
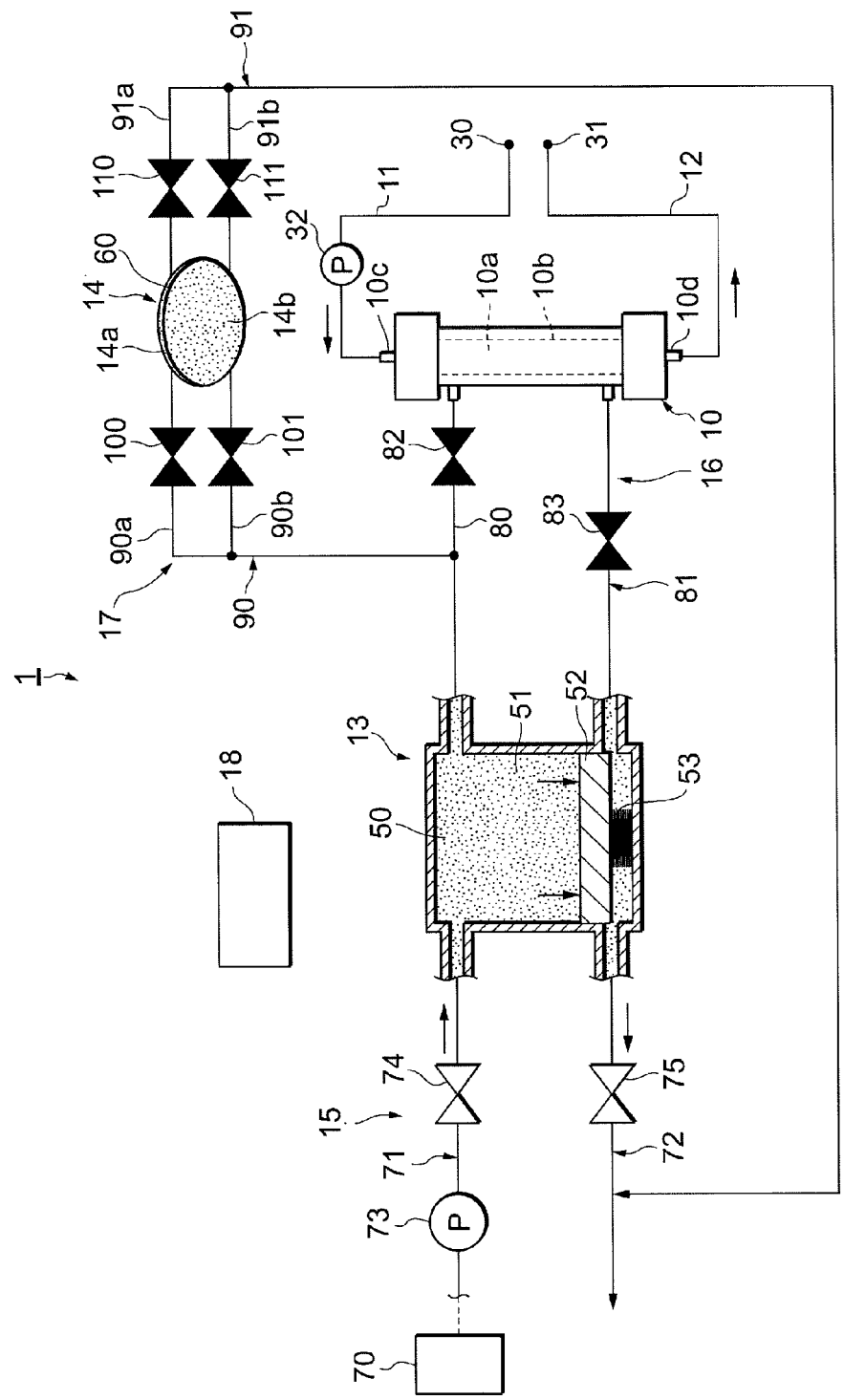
FIG. 5 is an explanatory diagram showing the state of the hemodialysis apparatus in the next first step.

Subsequently, as shown in FIG. 5, the on-off valves 82, 83 are once again closed and the on-off valves 74, 75 are opened, the new dialysate of the dialysate supply source 70 is supplied into the first chamber 50 of the quantitative vessel 13 by the pump 73, the partition wall 52 is pushed toward the second chamber 51 side against the resilience of the spring 53, the dialysate is filled in the first chamber 50 through the first circuit 71, and the water content in the blood and the waste dialysate in the second chamber 51 are discharged through the second circuit 72 (first step).

Figure 6:
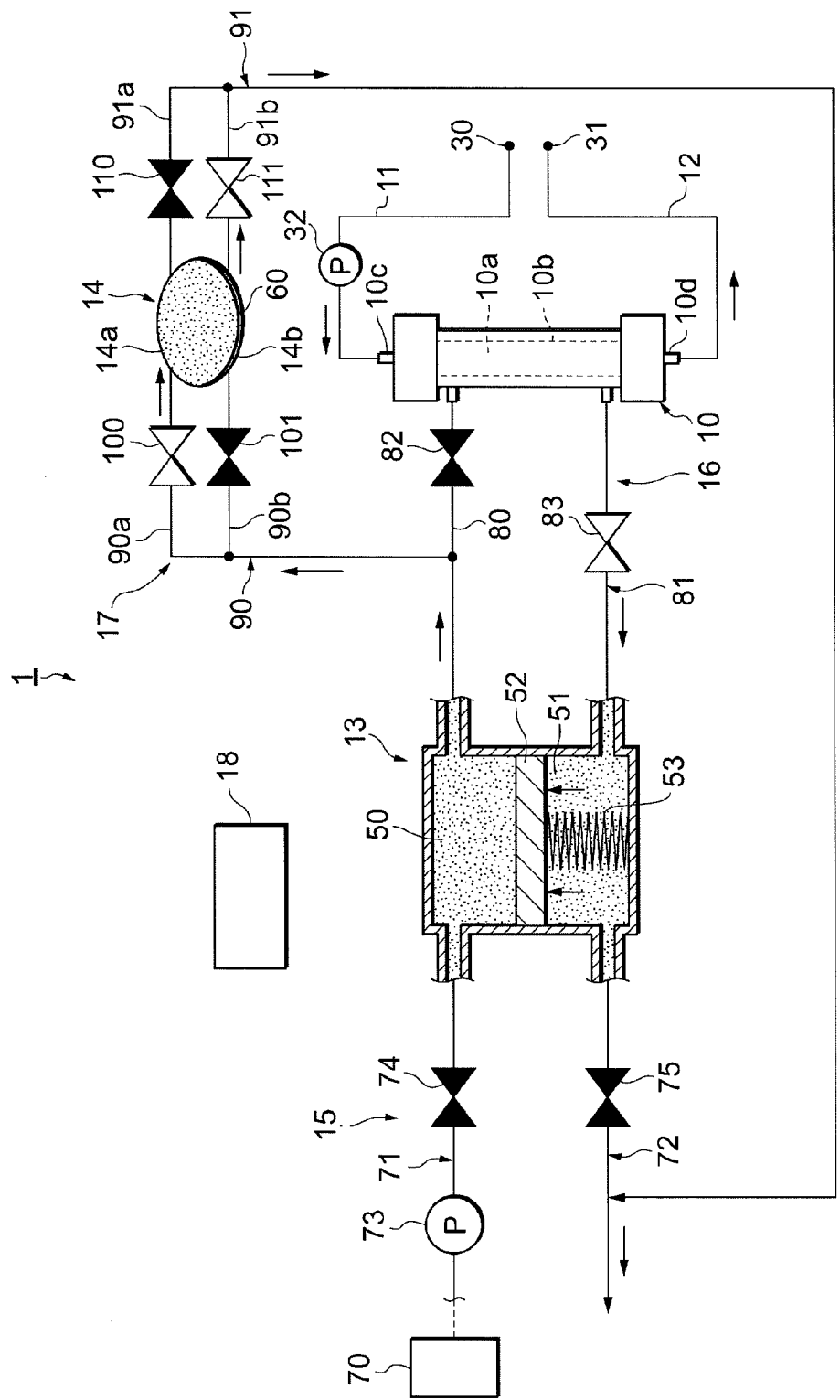
FIG. 6 is an explanatory diagram showing the state of the hemodialysis apparatus in the next second step.

Subsequently, for example, as shown in FIG. 6, the on-off valves 74, 75 are closed and the on-off valves 100, 111, 83 are opened, and the partition wall 52 moves to the first chamber 50 side due to the resilience of the spring 53. Consequently, the dialysate of a fixed quantity in the first chamber 50 is pushed out, and the dialysate is supplied to the first storage chamber 14a of the storage vessel 14 through the fifth circuit 90 (second case). Moreover, the second chamber 51 becomes a negative pressure due to the movement of the partition wall 52, the water content in the blood on the primary side 10a of the dialyzer 10 flows to the secondary side 10b based on the negative pressure, and the water content is discharged to the second chamber 51 through the fourth circuit 81 (second step). A predetermined amount of water content is thereby removed from the blood. The fluid removal in the foregoing case is an amount equal to the volume that increased in the second chamber 51 based on the movement of the partition wall 52 of the quantitative vessel 13, and this is the same as the amount equal to the amount that decreased in the first chamber 50; that is, the same as the amount of dialysate that was supplied to the first storage chamber 14a of the storage vessel 14 (amount equal to the maximum volume of the first storage chamber 14a).

Figure 7:
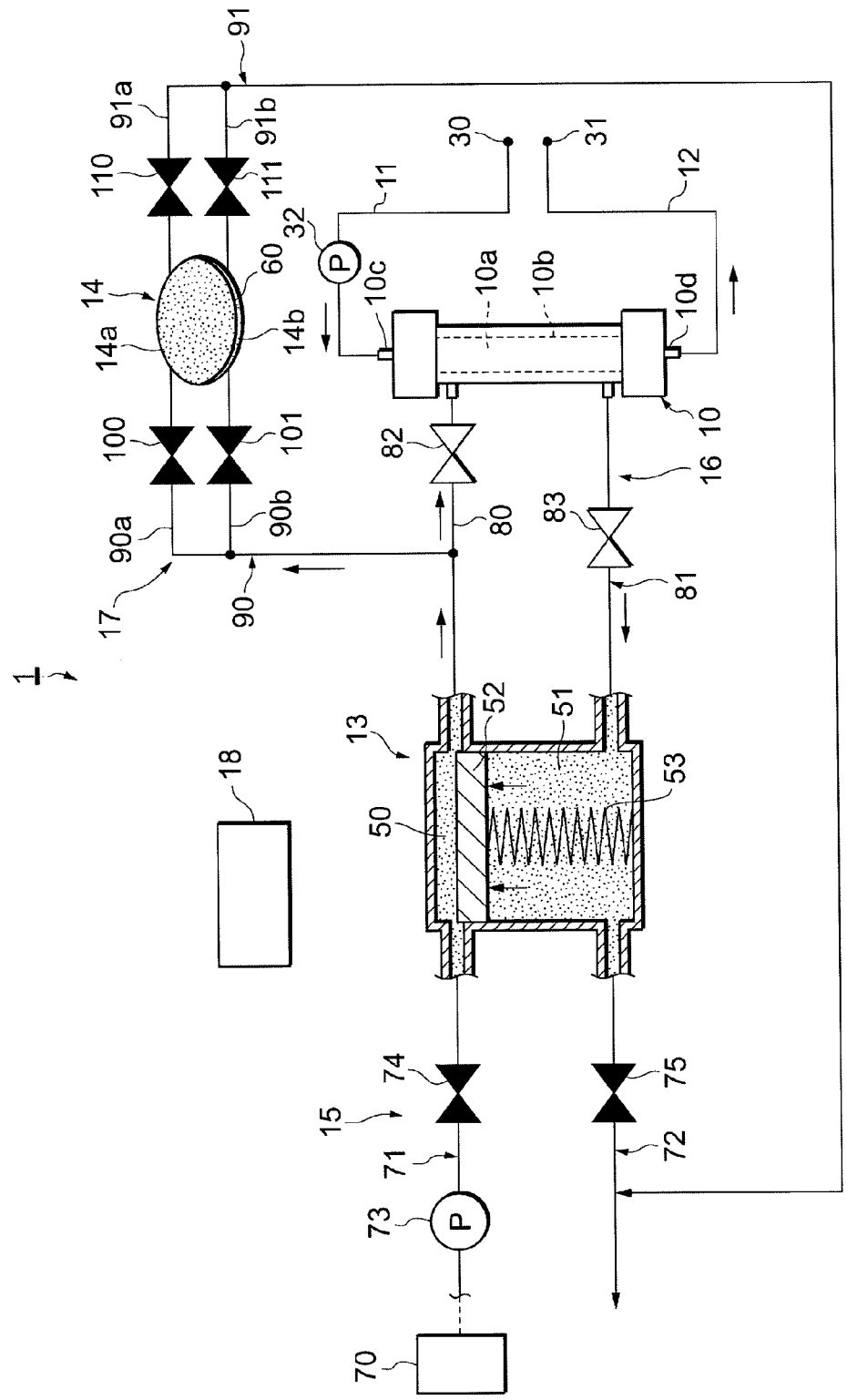
FIG. 7 is an explanatory diagram showing the state of the hemodialysis apparatus in the next third step.

When the first storage chamber 14a is filled with the dialysate and the water content flows into the second chamber 51, as shown in FIG. 7, the on-off valves 100, 111 are closed and the on-off valve 82 is opened. When the partition wall 52 of the quantitative vessel 13 moves further toward the first chamber 50 side due to the resilience of the spring 53, the remainder of the dialysate in the first chamber 50 is supplied to the secondary side 10b of the dialyzer 10 through the third circuit 80. In the dialyzer 10, the waste products that passed through the membrane from the patient's bloods on the primary side 10a are taken in the dialysate. Subsequently, the waste dialysate that passed through the dialyzer 10 flows into the second chamber 51 of the quantitative vessel 13 through the fourth circuit 81 (third step). Here, since the volume of the second chamber 51 increases in the amount that the volume of the first chamber 50 decreases due to the movement of the partition wall 52, the dialysate that is pushed out from the first chamber 50 to the dialyzer 10 side and the amount of waste dialysate that is introduced into the second chamber 51 will coincide.

Thereafter, the first step, the second step, and the third step are sequentially repeated as described above. Moreover, in the second step, the first case where the dialysate is supplied to the second storage chamber 14b side and the second case where the dialysate is supplied to the first storage chamber 14a side are alternately performed.

According to the embodiment described above, it is possible to displace the partition wall 52 of the quantitative vessel 13 to the first chamber 50 side, store the dialysate that was pushed out from the first chamber 50 in the storage vessel 14, and discharge the water content in the blood in the dialyzer 10 to the second chamber 51 based on the negative pressure that is consequently generated in the second chamber 51. Since it is thereby possible to discharge, to the second chamber 51, the water content of the blood in the same amount as the amount of dialysate (volume of the storage chamber of the storage vessel 14) that was discharged from the first chamber 50 to the storage vessel 14, an amount of water content removal from blood can be controlled with high precision based on easier control and mechanism. Moreover, since the dialysate can be supplied from the first chamber 50 to the dialyzer 10 through the third circuit 80 and the waste dialysate can be discharged from the dialyzer 10 to the second chamber 51 through the fourth circuit 81 by the displacement of the partition wall 52 to the first chamber 50 side, hemodialysis can also be performed appropriately.

Since the quantitative vessel 13 includes a spring 53 which applies resilience to the partition wall 52 for returning to the first chamber 50 side when the partition wall 52 is displaced to the second chamber 51 side, the displacement of the partition wall 52 of the quantitative vessel 13 can be performed based on resilience. Thus, for instance, a drive source that is needed for power feeding is not required, and the configuration and control of the apparatus can be simplified.

The storage vessel 14 includes a displaceable partition wall 60 which partitions the inside of the storage vessel into two storage chambers 14a, 14b, and the dialysate storage circuit 17 is configured to be capable of selectively supplying the dialysate in the first chamber 50 to the respective storage chambers 14a, 14b of the storage vessel 14, and of selectively discharging the dialysate in each of the storage chambers 14a, 14b. Consequently, since the dialysate can be alternately supplied to the two storage chambers 14a, 14b of the storage vessel 14 and, while supplying the dialysate to one storage chamber, the dialysate in the other storage chamber can be discharged, the dialysate can be continuously supplied to the storage vessel 14. Thus, ultrafiltration from the blood can be performed continuously, and ultrafiltration can be performed efficiently.

Since the dialysate storage circuit 17 is configured to be capable of discharging the dialysate in each of the storage chambers 14a, 14b to the second circuit 72 of the dialysate exchange circuit 15, the circuit for discharging the dialysate in the storage vessel 14 can be simplified. Note that the dialysate storage circuit 17 can also be configured to be capable of discharging the dialysate in the respective storage chambers 14a, 14b to the dialysate supply source 70.

In the foregoing embodiment, the control unit 18 sequentially and repeatedly implements a first step of supplying the dialysate to the first chamber 50 of the quantitative vessel 13 through the dialysate exchange circuit 15, displacing the partition wall 52 of the quantitative vessel 13 to the second chamber 51 side, and discharging the waste dialysate in the second chamber 51 of the quantitative vessel 13 through the dialysate exchange circuit 15; a second step of displacing the partition wall 52 of the quantitative vessel 13 to the first chamber 50 side in a state where blood is being supplied to the primary side 10a of the dialyzer 10 to supply a part of the dialysate in the first chamber 50 to the storage vessel 14 through the dialysate storage circuit 17, and discharging the water content of the blood from the secondary side 10b of the dialyzer 10 to the second chamber 51 through the dialysate supply circuit 16 by utilizing a negative pressure of the second chamber 51 that has been generated by the displacement of the partition wall 52 to the first chamber 50 side; and a third step of supplying the remaining dialysate in the first chamber 50 to the secondary side 10b of the dialyzer 10 through the dialysate supply circuit 16 and discharging the waste dialysate from the secondary side 10b of the dialyzer 10 to the second chamber 51 by the displacement of the partition wall 52 to the first chamber 50 side. It is thereby possible to efficiently perform dialysis and ultrafiltration while controlling the fluid removal with high precision. Note that the first step may be implemented in a state where the blood is passing through the primary side 10*a* of the dialyzer 10, or in a state where the blood is not passing therethrough.

Figure 8:
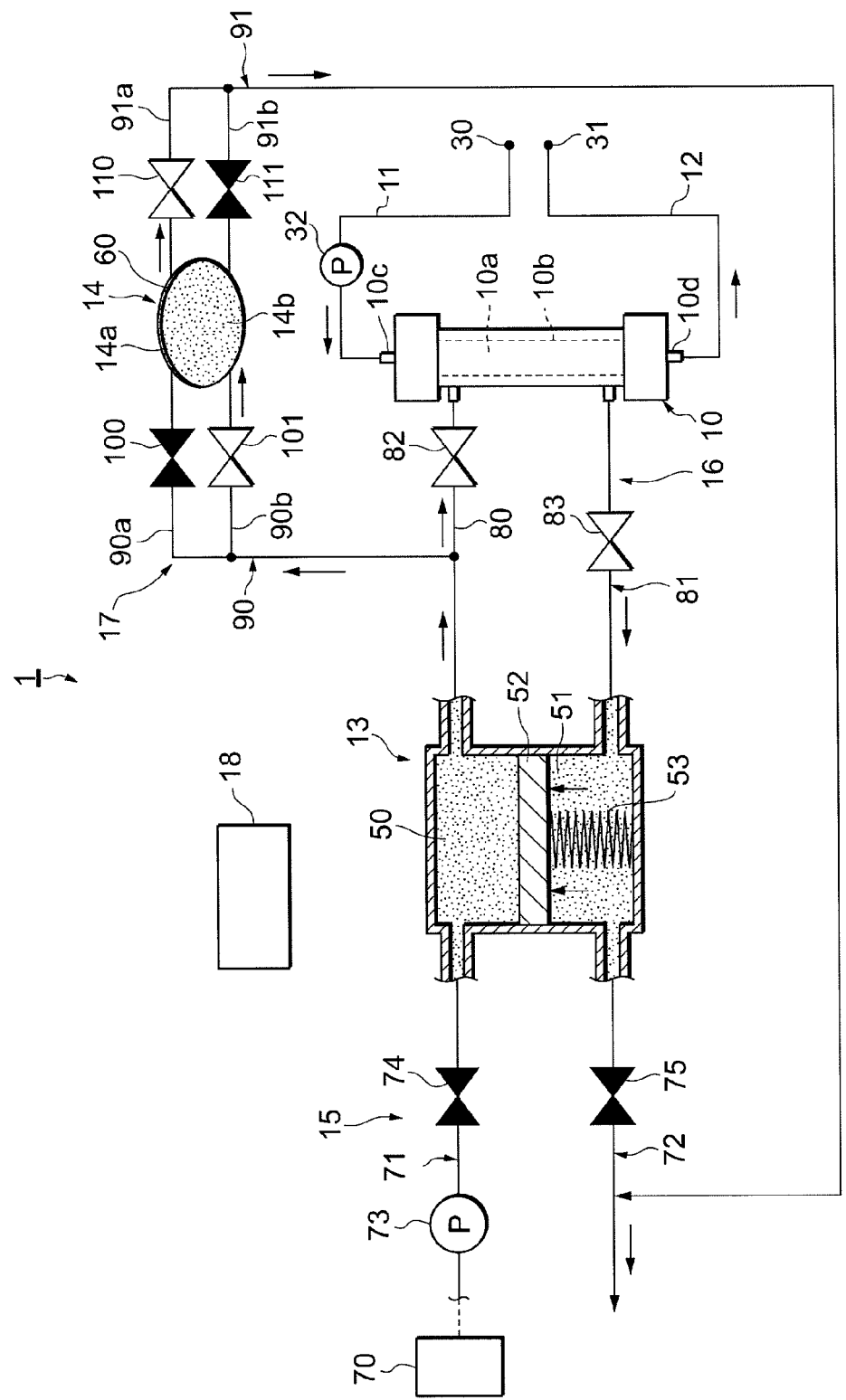
FIG. 8 is an explanatory diagram showing the state of the hemodialysis apparatus in the case of simultaneously performing a part of the second step and a part of the third step.

Moreover, in the foregoing embodiment, although the control unit 18 implemented the third step after the second step, a part of the second step and a part of the third step may also be implemented simultaneously. For example, as shown in FIG. 8, after a new dialysate is filled in the first chamber 50 of the quantitative vessel 13, the on-off valves 74, 75 are closed, and the on-off valve 82 is opened in addition to the on-off valves 101, 110, 83. In addition, the partition wall 52 moves to the first chamber 50 side due to the resilience of the spring 53 of the quantitative vessel 13, the dialysate of a fixed quantity in the first chamber 50 is pushed out, a part of the dialysate is supplied, for example, to the second storage chamber 14*b* of the storage vessel 14 through the fifth circuit 90, and the remaining dialysate is supplied to the secondary side 10*b* of the dialyzer 10 through the third circuit 80. The dialysate that was supplied to the secondary side 10*b* of the dialyzer 10 takes in the waste products from the blood and becomes a waste dialysate, and this is returned to the second chamber 51 through the fourth circuit 81.

Here, since a part of the dialysate, which was pushed out as a result of the partition wall 52 moving to the first chamber 50 side, is stored in the second storage chamber 14*b*, the supplied amount of dialysate to the dialyzer 10 decreases by that much, and a negative pressure is generated in the second chamber 51. The water content in the blood on the primary side 10*a* of the dialyzer 10 flows into the secondary side 10*b* due to the consequent negative pressure of the second chamber 51, and the water content is discharged to the second chamber 51 through the fourth circuit 81. In other words, the water content in the blood corresponding to the difference between the overall amount of dialysate that was discharged from the first chamber 50 of the quantitative vessel 13 and the amount of waste dialysate that was returned to the second chamber 51 is discharged to the second chamber 51. A predetermined amount of water content is thereby removed from the blood. When the second storage chamber 14*b* is filled with the dialysate, the on-off valve 101 is closed, and, after the movement of the partition wall 52 to the first chamber 50 side is complete, the on-off valve 82 and the on-off valve 83 are closed.

In the foregoing case also, dialysis and ultrafiltration can be performed efficiently while controlling the fluid removal with high precision.

Note that, in the foregoing examples, the third step was performed after the second step or the second step and the third step were simultaneously started, but it will suffice so as long as at least one of either the second step or the third step, and the first step are alternately performed. For example, the start timing and the end timing of the second step and the third step may be a timing other the foregoing examples. Moreover, the second step may be started and ended while the third step is being performed, or the third step may be started and ended while the second step is being performed.

Moreover, upon repeating the first step and the second and third steps in the foregoing embodiment, there may be cases where the second step is not implemented, and the first step and the third step are alternately implemented. In the foregoing case, in the first step, the dialysate is supplied to the first chamber 50 of the quantitative vessel 13 through the first circuit 71, the partition wall 52 of the quantitative vessel 13 is displaced to the second chamber 51 side, and the dialysate and the water content in the blood in the second chamber 51 are discharged through the second circuit 72. Subsequently, in the third step, in a state where the blood is passing through the primary side 10*a* of the dialyzer 10, the partition wall 52 is displaced to the first chamber 50 side, the dialysate in the first chamber 50 is pushed out and supplied to the secondary side 10*b* of the dialyzer 10, and the dialysate that passed through the dialyzer 10 is discharged to the second chamber 51. The first step and the third step are sequentially repeated, the second step is implemented once every predetermined number of times of such repetition, and the water content contained in the blood is thereby removed. Consequently, the fluid removal can be more strictly adjusted.

Figure 9:
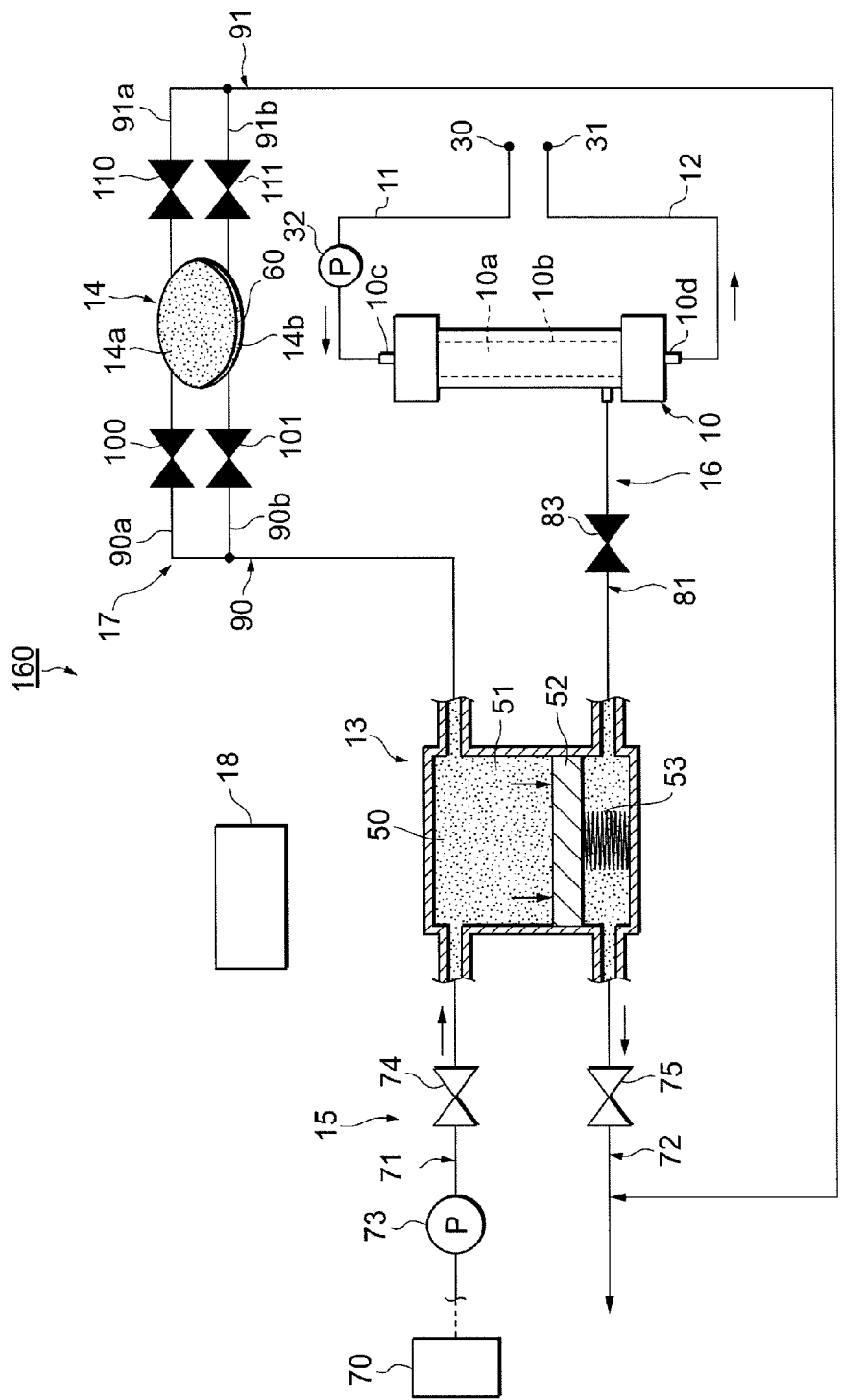
FIG. 9 is an explanatory diagram showing the state of the water content removal system in the first step.

The foregoing embodiment applied the present invention to a hemodialysis apparatus 1, but the present invention from a different perspective may also be a water content removal system which removes the water content of blood. In the foregoing case, the water content removal system may include the function of performing dialysis as with the hemodialysis apparatus described in the foregoing embodiment, or may be a type which only performs ultrafiltration as shown below. For example, as shown in FIG. 9, the water content removal system 160 includes a separator 10 through which blood passes and which separates the water content from the blood, a quantitative vessel 13 including a displaceable partition wall which partitions the inside of the vessel into a first chamber and a second chamber, a storage vessel 14 which stores a predetermined fluid, a first circuit 71 which supplies the fluid to the first chamber 50 of the quantitative vessel 13, a second circuit 72 which discharges the water content of the blood in the second chamber 51 of the quantitative vessel 13, a third circuit 90 which supplies the fluid in the first chamber 50 of the quantitative vessel 13 to the storage vessel 14, and a fourth circuit 81 which discharges the water content from the separator 10 to the second chamber 51. The quantitative vessel 13 is configured to be capable of displacing the partition wall 52 to the first chamber 50 side to push out the fluid from the first chamber 50 and store the fluid in the storage vessel 14 through the third circuit 90, and of discharging the water content from the separator 10 to the second chamber 51 through the fourth circuit 81 by utilizing a negative pressure of the second chamber 51 that has been generated by the displacement of the partition wall 52 to the first chamber 50 side. Note that, since the water content removal system 160 is configured basically the same as the foregoing hemodialysis apparatus 1, the same reference numeral is given to the members that are configured the same as in the hemodialysis apparatus 1, and the explanation thereof is omitted.

Figure 10:
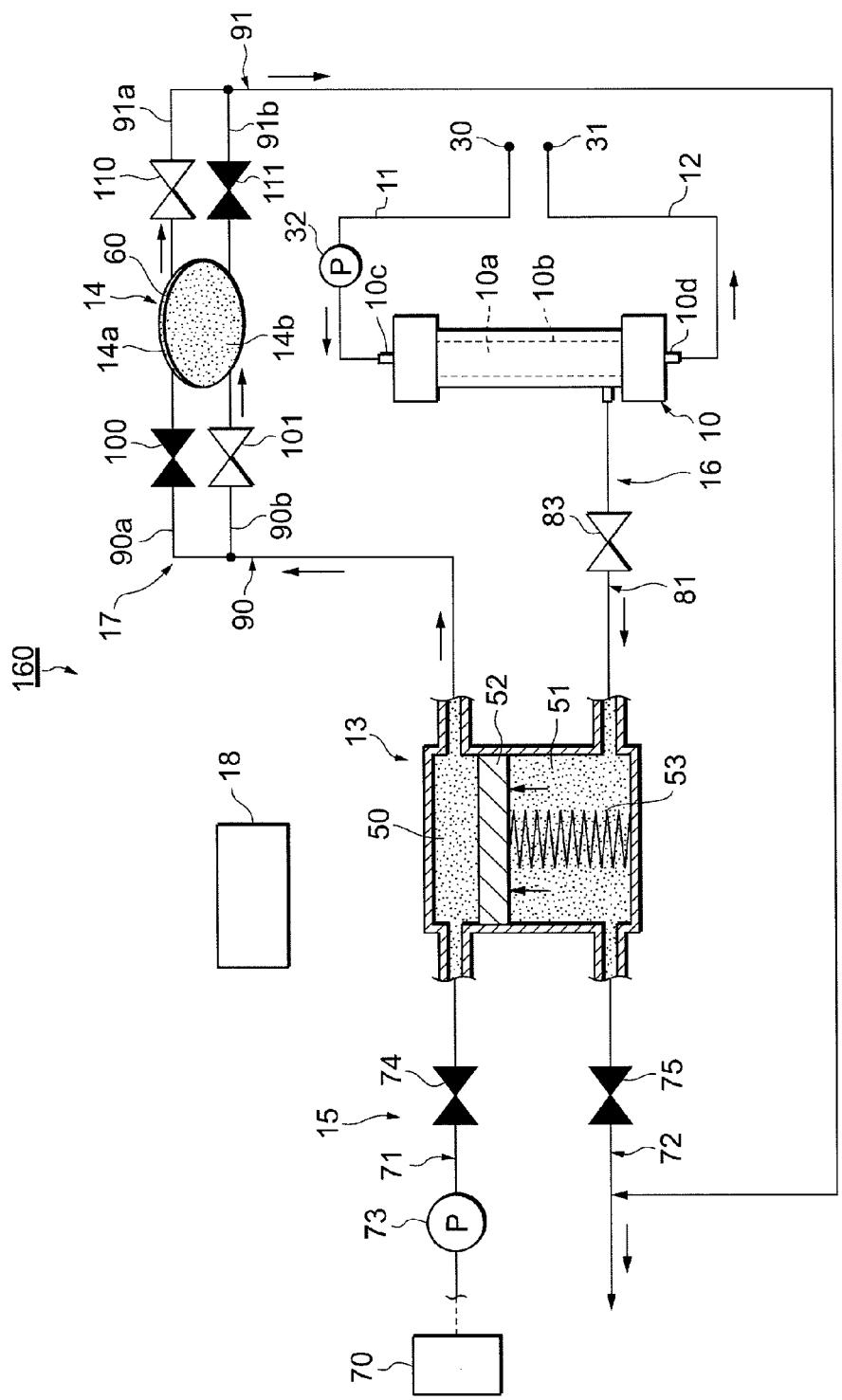
FIG. 10 is an explanatory diagram showing the state of the water content removal system in the second step.

The ultrafiltration treatment using the water content removal system 160 is performed by operating the control unit 18. For example, as shown in FIG. 9, the on-off valves 74, 75 are opened and the on-off valves 100, 101, 110, 111, 83 are closed, a dialysate as a predetermined fluid is supplied to the first chamber 50 of the quantitative vessel 13 through the first circuit 71, the partition wall 52 of the quantitative vessel 13 is displaced to the second chamber 51 side, and the existing water content contained in the blood in the second chamber 51 is discharged outside through the second circuit 72 (first step). Here, the spring 53 of the quantitative vessel 13 is compressed. Subsequently, as shown in FIG. 10, the on-off valves 74, 75 are closed and the on-off valves 101, 110, 83 are opened, and, in a state where the blood is passing through the primary side 10*a* of the separator 10, the partition wall 52 of the quantitative vessel 13 is displaced to the first chamber 50 side due to the resilience of the spring 53, and the dialysate in the first chamber 50 is pushed out and stored in the second storage chamber 14*b* of the storage vessel 14 through the third circuit 90. Here, the partition wall 60 moves and the existing dialysate in the first storage chamber 14*a* is discharged through the sixth circuit 91 (first case). Moreover, the water content of the blood is discharged from the separator 10 to the second chamber 51 through the fourth circuit 81 based on the negative pressure that is generated in the second chamber 51 when the partition wall 52 of the quantitative vessel 13 is displaced to the first chamber 50 side (second step). The fluid removal in the foregoing case is an amount equal to the volume that increased in the second chamber 51 based on the movement of the partition wall 52 of the quantitative vessel 13, and this is the same as the amount equal to the amount that decreased in the first chamber 50; that is, the same as the amount of dialysate that was supplied to the second storage chamber 14*b* of the storage vessel 14 (amount equal to the maximum volume of the second storage chamber 14*b*).

Figure 11:
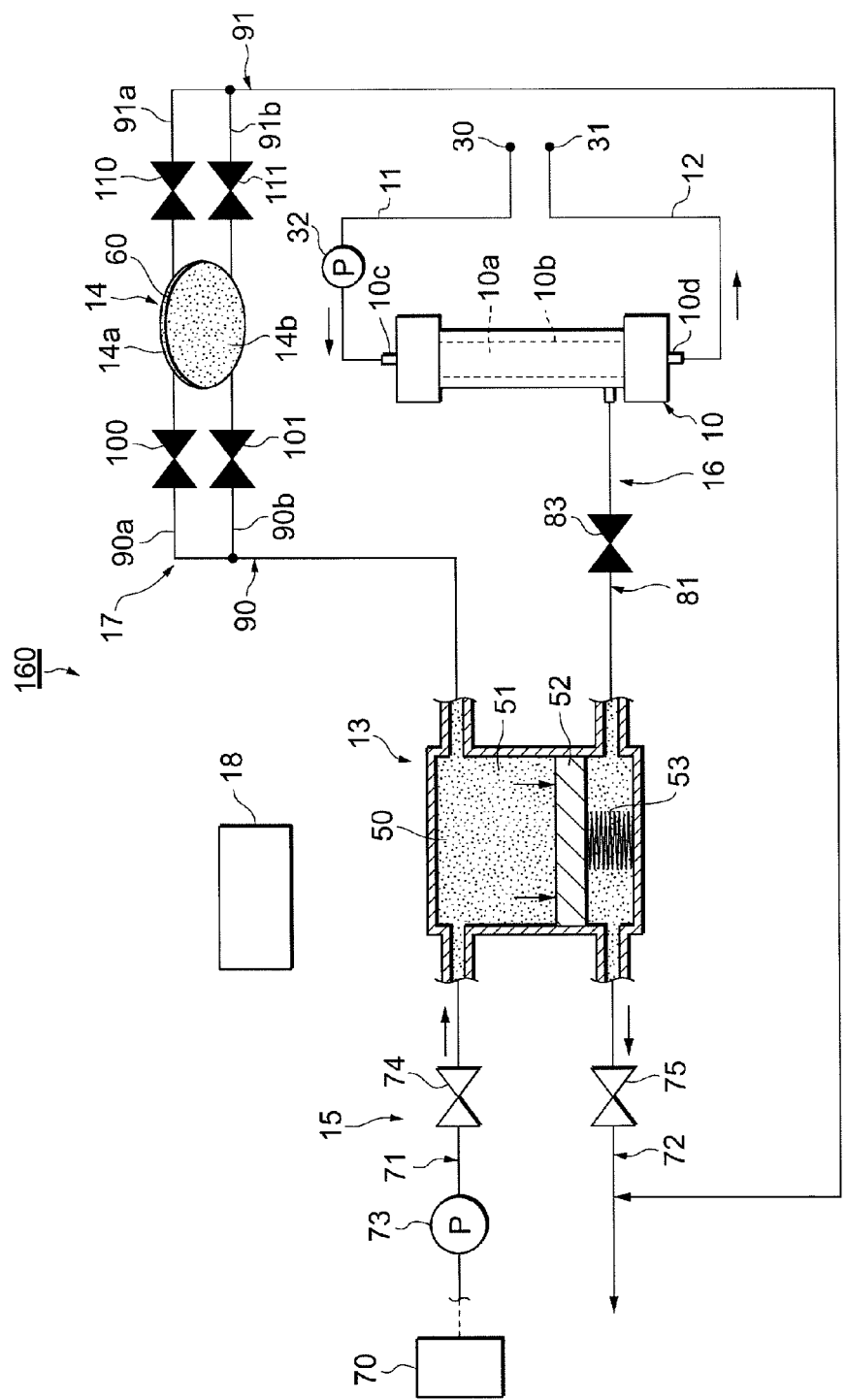
FIG. 11 is an explanatory diagram showing the state of the water content removal system in the next first step.
Figure 12:
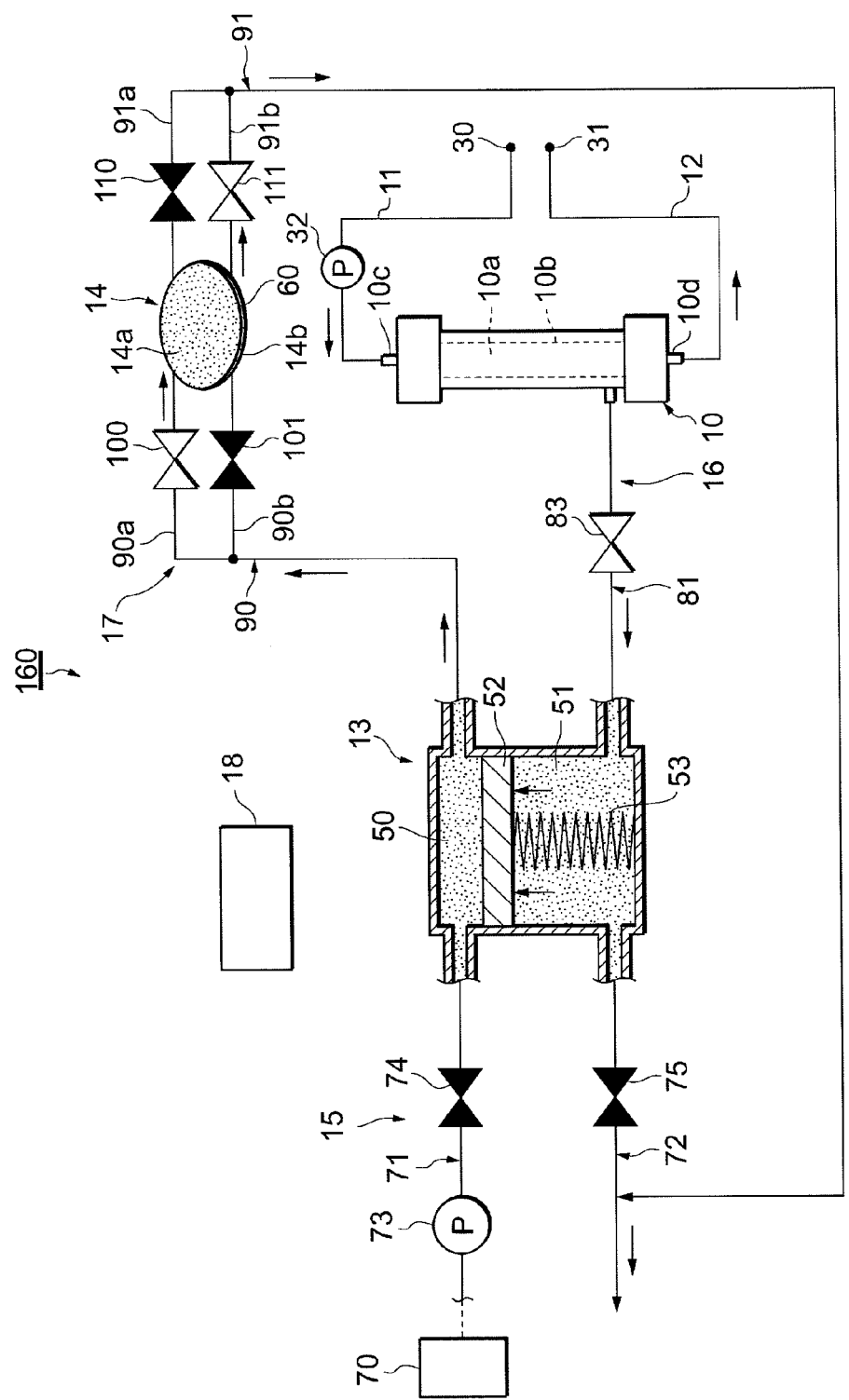
FIG. 12 is an explanatory diagram showing the state of the water content removal system in the next second step.

Subsequently, as shown in FIG. 11, the on-off valves 74, 75 are opened once again and the on-off valves 101, 110, 83 are closed, the dialysate is supplied to the first chamber 50 of the quantitative vessel 13 through the first circuit 71, the partition wall 52 of the quantitative vessel 13 is displaced to the second chamber 51 side, and the water content in the second chamber 51 is discharged outside through the second circuit 72 (first step). Subsequently, as shown in FIG. 12, the on-off valves 74, 75 are closed and the on-off valves 100, 111, 83 are opened, and, in a state where the blood is passing through the primary side 10*a* of the separator 10, the partition wall 52 of the quantitative vessel 13 is displaced to the first chamber 50 side due to the resilience of the spring 53, and the dialysate in the first chamber 50 is pushed out and stored in the first storage chamber 14*a* of the storage vessel 14 through the third circuit 90. Here, the partition wall 60 moves and the dialysate in the second storage chamber 14*b* is discharge through the sixth circuit 91 (second case). Moreover, the water content of the blood is discharged from the separator 10 to the second chamber 51 through the fourth circuit 81 based on the negative pressure that is generated in the second chamber 51 when the partition wall 52 of the quantitative vessel 13 is displaced to the first chamber 50 side (second step). Thereafter, the first step and the second step are alternately implemented as described above. In the second step, the first case and the second case are alternately implemented.

According to this embodiment, since it is thereby possible to discharge, to the second chamber 51, the water content of the blood in the same amount as the amount of dialysate (volume of the storage chambers 14*a*, 14*b* of the storage vessel 14) that was discharged from the first chamber 50 to the storage vessel 14, fluid removal from blood can be controlled with high precision based on easier control and mechanism. Moreover, since the dialysate can be alternately supplied to the two storage chambers 14*a*, 14*b* of the storage vessel 14, and, while supplying the dialysate to one storage chamber, the dialysate in the other storage chamber can be discharged, the dialysate can be continuously supplied to the storage vessel 14. Thus, ultrafiltration from the blood can be performed continuously, and ultrafiltration can be performed efficiently.

Note that, in this embodiment, dialysate was used as the fluid to be supplied to the first chamber 50 of the quantitative vessel 13 and the storage vessel 14, it may also be other fluids such as saline, water or the like.

For example, in the foregoing embodiments, the partition wall 52 of the quantitative vessel 13 generated resilience based on a spring 53, but the partition wall 52 can also generate resilience by using other resilience application devices configured from an elastic diaphragm or the like. Moreover, without using resilience, the partition wall 52 can be driven with other drive sources. Moreover, the partition wall 52 is not limited to having a piston shape, and can also be configured in the form of a membrane such as a diaphragm.

With the hemodialysis apparatus 1 described above, the quantitative vessel 13, the storage vessel 14, at least a part of the dialysate exchange circuit 15, at least a part of the dialysate supply circuit 16, and at least a part of the dialysate storage circuit 17 may be formed on a cassette unit which can be freely attached to and detached from the apparatus body. Moreover, with the hemodialysis apparatus 1, at least a part of the blood removal-side circuit 11 and at least a part of the retransfusion-side circuit 12 may be formed on a cassette unit which can be freely attached to and detached from the apparatus body.

Figure 13:
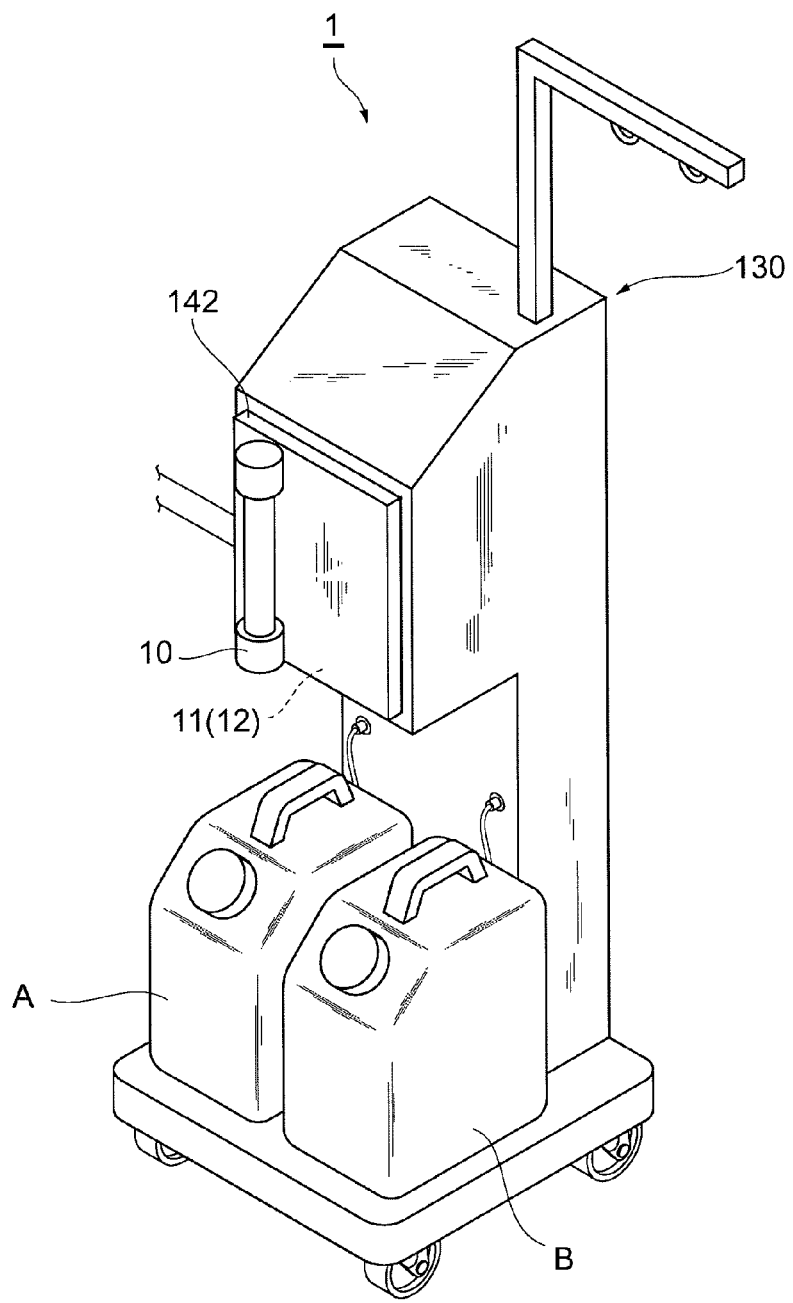
FIG. 13 is a perspective view of the front side showing an outline of the configuration of the hemodialysis apparatus.
Figure 14:
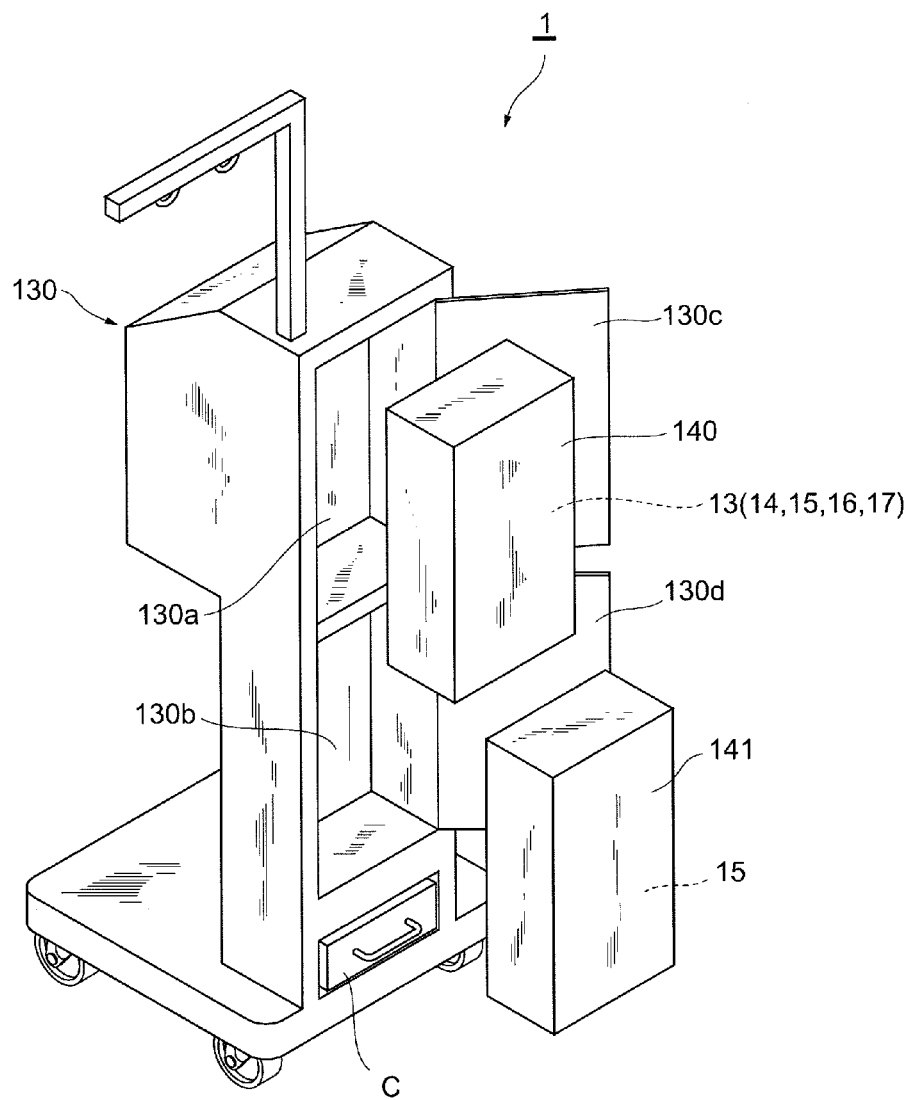
FIG. 14 is a perspective view of the rear side showing an outline of the configuration of the hemodialysis apparatus.

An example of the foregoing case is now explained with reference to the drawings. FIG. 13 and FIG. 14 are perspective views showing an outline of the configuration of the hemodialysis apparatus 1 according to this embodiment.

The hemodialysis apparatus 1 includes, for example, a plurality of (for instance, three) cassette units 140, 141, 142 provided so that they can be freely attached to and detached from the apparatus body 130. As shown in FIG. 14, the first cassette unit 140 and the second cassette unit 141 are formed, for example, in a substantially rectangular shape. For instance, two cassette housing parts 130*a*, 130*b* arranged vertically are provided to the rear side of the apparatus body 130, and the first cassette unit 140 and the second cassette unit 141 can be housed in the cassette housing parts 130*a*, 130*b* and then mounted on the apparatus body 130. Openable/closable doors 130*c*, 130*d* capable of hermetically sealing the inside are provided to the cassette housing parts 130*a*, 130*b*. Note that the apparatus body 130 is equipped with dialysate stock solution tanks A, B (shown in FIG. 13) and a diluted solution tank C (shown in FIG. 14). The dialysate stock solution tanks A, B and the diluted solution tank C belong, for example, to the dialysate supply source 70.

As shown in FIG. 13, the third cassette unit 142 is formed, for example, in a plate shape, and is configured, for example, so that it can be freely attached to and detached from the front face of the apparatus body 130.

Figure 15:
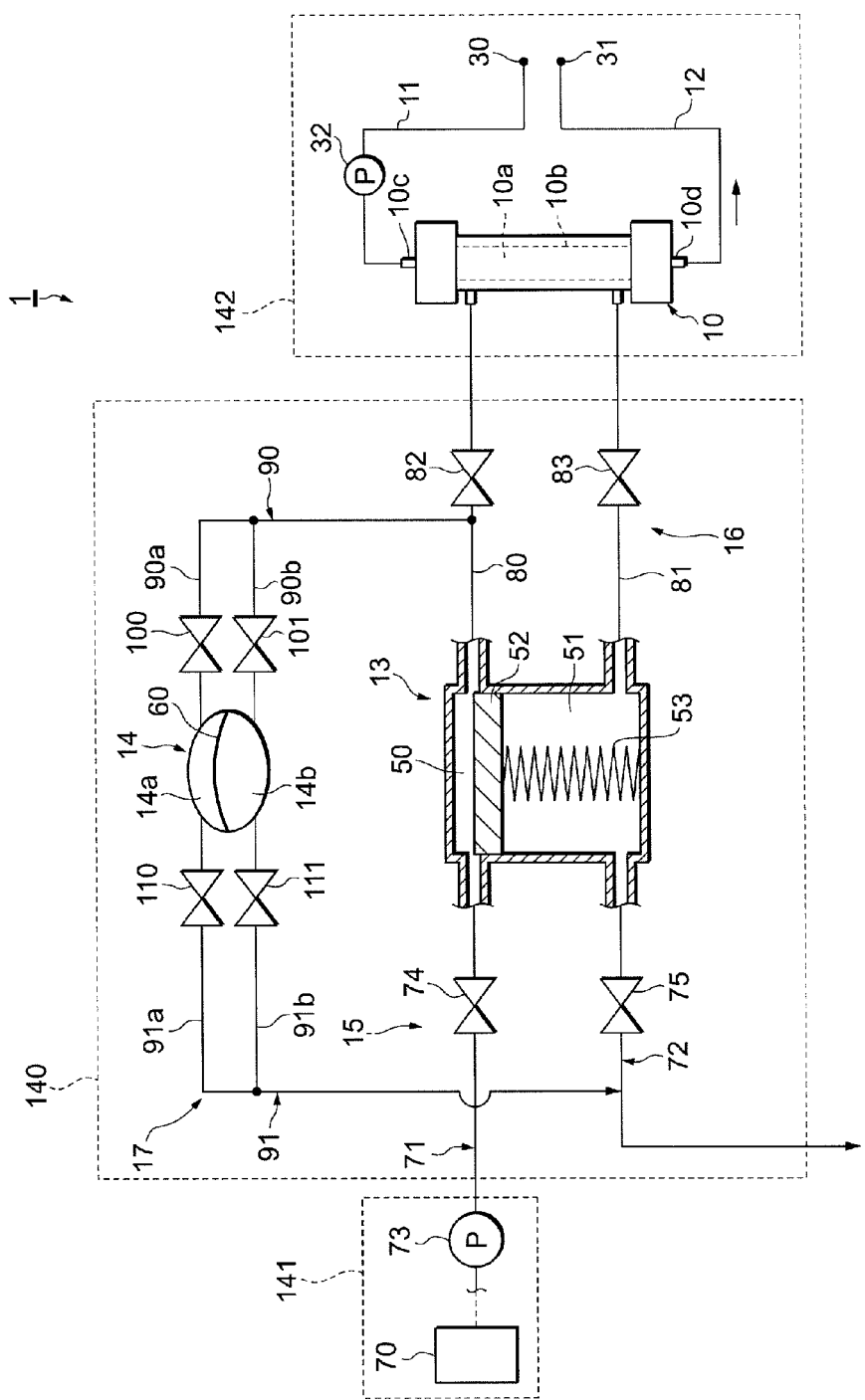
FIG. 15 is an explanatory diagram showing the configuration of the cassette unit of the hemodialysis apparatus.

For example, as shown FIG. 15, formed on the first cassette unit 140 are a quantitative vessel 13, a storage vessel 14, portions other than the dialysate supply source 70 and the pump 73 within the dialysate exchange circuit 15, a dialysate supply circuit 16, and a dialysate storage circuit 17.

Certain portions of the dialysate supply source 70 and the pump 73 within the dialysate exchange circuit 15 are formed on the second cassette unit 141. For example, with the first cassette unit 140 and the second cassette unit 141, the vessels 13, 14 and the circuits 15, 16, 17 are formed on the inside or surface thereof via DSI (Die Slide Injection) molding.

A blood removal-side circuit 11 and a retransfusion-side circuit 12 are formed on the third cassette unit 142. The dialyzer 10 can be attached to and detached from the third cassette unit 142.

During the maintenance of the foregoing hemodialysis apparatus 1, for instance, the cassette units 140 to 142 are removed from the apparatus body 130 as needed, and replaced with new cassette units 140 to 142.

According to this embodiment, the cassette units 140 to 142 can be removed from the apparatus body 130, and the maintenance of the hemodialysis apparatus 1 can be performed by replacing the cassette units 140 to 142 with new cassette units. Consequently, even a person without any professional knowledge, skill or experience can perform the maintenance of the hemodialysis apparatus 1 easily, and the quality of maintenance can also be ensured. Thus, the patient can perform ongoing hemodialysis treatment by using the hemodialysis apparatus 1 even at home or in a depopulated area and, for instance, the patient's QOL can be improved.

Note that, in this embodiment, three cassette units 140 to 142 were provided to the hemodialysis apparatus 1, but the quantity thereof can be arbitrarily selected. For example, the various vessels and circuits of the first cassette unit 140 and the second cassette unit 141 can also be formed on a single cassette unit.

In the foregoing embodiment, in each of the valves, for instance, the on-off valves 74, 75, 82, 83, 100, 101, 110, 111 (hereinafter collectively referred to as the "on-off valve V") for supplying and discharging the fluid to and from the quantitative vessel 13 and the storage vessel 14, a portion that comes into contact with the fluid may be formed on the cassette unit and a portion that does not come into contact with the fluid may be formed on the apparatus body.

Figure 16:
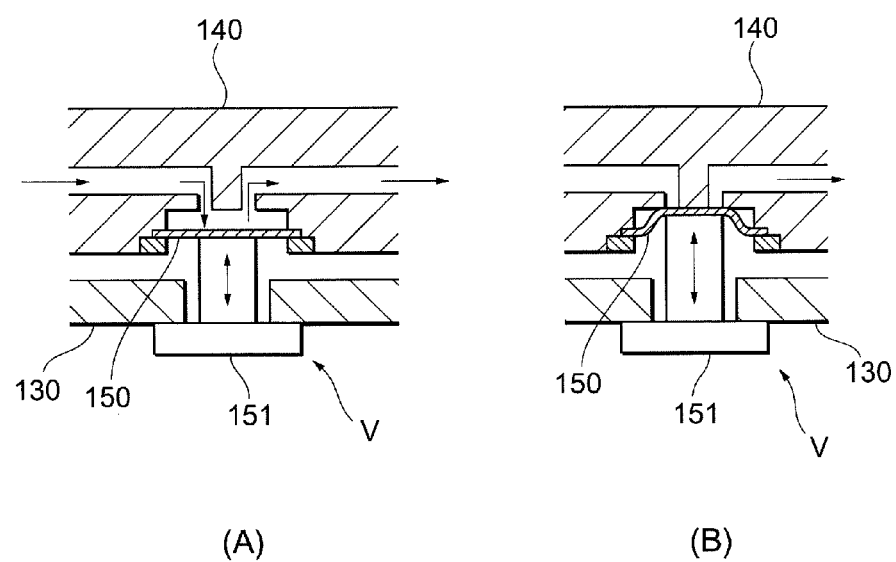
FIG. 16(A) is an explanatory diagram showing an example of the configuration of the on-off valve when it is open.
FIG. 16(B) is an explanatory diagram showing an example of the configuration of the on-off valve when it is closed.

In the foregoing case, the on-off valve V is configured so that it can be separated into a portion that comes into contact with the fluid and a portion that does not come into contact with the fluid. For example, the on-off valve V includes, as shown in FIG. 16, a deformable membrane 150 which comes into contact with the fluid and moves, and a pressing member 151 which moves the deformable membrane 150 without coming into contact with the fluid. The deformable membrane 150 is, for example, a flexible object (diaphragm) that is exposed in the fluid channel of the respective circuits, and the pressing member 151 is configured, for example, a solenoid or the like that moves, for instance, based on electromagnetic action, and can press the deformable membrane 150 from the outside and open/close the fluid channel of the respective circuits. The deformable membrane 150 that comes into contact with the fluid is provided to the first cassette unit 140 side, and the pressing member 151 that does not come into contact with the fluid is provided to the apparatus body 130 side. FIG. 16(A) shows a state where the deformable membrane 150 is lowered and the on-off valve V is opened, and FIG. 16(B) shows a state where the deformable membrane 150 is raised and the on-off valve V is closed.

The pressing member 151 is provided, for example, by being exposed to the surface of the cassette housing part 130a of the apparatus body 130, and the deformable membrane 150 is provided by being exposed to the surface of the first cassette unit 140. When the first cassette unit 140 is housed in the cassette housing part 130a, the pressing member 151 on the apparatus body 130 side and the deformable membrane 150 on the first cassette unit 140 side deformable membrane 150 become fitted together, and thereby form the on-off valve V.

According to the foregoing embodiment, since the portion of the on-off valve V that comes into contact with the fluid is provided to the first cassette unit 140 side and the portion that does not come into contact with the fluid is provided to the apparatus body 130 side, for instance, the portion that will become contaminated or deteriorated easily can be replaced together with the cassette unit 140, and the portion that will not become contaminated or deteriorated easily or the expensive portion can be left on the apparatus body 130. Thus, the maintenance can be performed effectively and, for example, the maintenance cost of the hemodialysis apparatus 1 can be reduced.

Note that the structure of the on-off valve V is not limited to the above, and may also be of a different structure.

The preferred embodiments of the present invention were explained above with reference to the appended drawings, but the present invention is not limited to such examples. It is obvious that a person skilled in the art can conceive various modified examples or revised examples within the nature of the concept described in the claims, and it should be understood that such modified examples and revised examples also belong within the technical scope of the present invention as a matter of course.

The present invention is useful upon controlling the fluid removal from the blood with high precision based on easy control and fluid removal.

REFERENCE SYMBOLS

1 hemodialysis apparatus
10 dialyzer
11 blood removal-side circuit
12 retransfusion-side circuit
13 quantitative vessel
14 storage vessel
14a first storage chamber
14b second storage chamber
15 dialysate exchange circuit
16 dialysate supply circuit
17 dialysate storage circuit
18 control unit
30, 31 needle part
50 first chamber
51 second chamber
52 partition wall
53 spring
60 partition wall
70 dialysate supply source
71 first circuit
72 second circuit
73 pump
74, 75 on-off valve
80 third circuit
81 fourth circuit
82, 83 on-off valve
90 fifth circuit
91 sixth circuit
100, 101 on-off valve
110, 111 on-off valve
130 apparatus body
140 to 142 cassette unit

We claim:

1. A hemodialysis apparatus, comprising:
a dialyzer;
a vessel including a displaceable partition wall which partitions the inside of the vessel into a first chamber and a second chamber;
a storage vessel which stores a dialysate;
a dialysate exchange circuit which supplies the dialysate to the first chamber and discharges a waste dialysate in the second chamber to the outside by the consequent displacement of the partition wall to the second chamber side;
a dialysate supply circuit which supplies the dialysate in the first chamber to the dialyzer and discharges the waste dialysate from the dialyzer to the second chamber by the displacement of the partition wall to the first chamber side;
a dialysate storage circuit which supplies the dialysate in the first chamber to the storage vessel by the displacement of the partition wall to the first chamber side; and
a control unit which implements a first control of supplying the dialysate to the first chamber of the vessel through the dialysate exchange circuit, displacing the partition wall of the vessel to the second chamber side, and discharging the waste dialysate in the second chamber of the vessel through the dialysate exchange circuit, a second control of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side, and a third control of supplying the dialysate in the first chamber to the dialyzer through the dialysate supply circuit and discharging the waste dialysate from the dialyzer to the second chamber by the displacement of the partition wall to the first chamber side, wherein the control unit alternately implements at least either the second control or the third control, and the first control.

2. The hemodialysis apparatus according to claim 1, wherein the vessel includes a resilience application device which applies resilience to the partition wall for returning to the first chamber side when the partition wall is displaced to the second chamber side.

3. A hemodialysis apparatus, comprising:
a dialyzer;
a vessel including a displaceable partition wall which partitions the inside of the vessel into a first chamber and a second chamber;
a storage vessel which stores a dialysate;
a dialysate exchange circuit which supplies the dialysate to the first chamber and discharges a waste dialysate in the second chamber to the outside by the consequent displacement of the partition wall to the second chamber side;
a dialysate supply circuit which supplies the dialysate in the first chamber to the dialyzer and discharges the waste dialysate from the dialyzer to the second chamber by the displacement of the partition wall to the first chamber side;
a dialysate storage circuit which supplies the dialysate in the first chamber to the storage vessel by the displacement of the partition wall to the first chamber side,
wherein the storage vessel includes a displaceable partition wall which partitions the inside of the storage vessel into two storage chambers, and
the dialysate storage circuit is configured to be capable of selectively supplying the dialysate in the first chamber to the respective storage chambers of the storage vessel, and of selectively discharging the dialysate in each of the storage chambers.

4. The hemodialysis apparatus according to claim 3, wherein the dialysate storage circuit is configured to be capable of discharging the dialysate in each of the storage chambers to the dialysate exchange circuit.

5. The hemodialysis apparatus according to claim 1, wherein the vessel, the storage vessel, at least a part of the dialysate exchange circuit, at least a part of the dialysate supply circuit, and at least a part of the dialysate storage circuit are formed on a cassette unit which can be freely attached to and detached from the hemodialysis apparatus.

6. The hemodialysis apparatus according to claim 1, further comprising:
a blood removal-side circuit which supplies blood of a living subject to the dialyzer; and
a retransfusion-side circuit which returns the blood in the dialyzer to the living subject,
wherein at least a part of the blood removal-side circuit and at least a part of the retransfusion-side circuit are formed on a cassette unit which can be freely attached to and detached from the hemodialysis apparatus.

7. The hemodialysis apparatus according to claim 5, wherein, in a valve for supplying and discharging the fluid to and from the vessel and the storage vessel, a portion that comes into contact with the fluid is formed on the cassette unit and a portion that does not come into contact with the fluid is formed on a body of the hemodialysis apparatus.

8. A method of operating a hemodialysis apparatus,
the hemodialysis apparatus including:
a dialyzer;
a vessel including a displaceable partition wall which partitions the inside of the vessel into a first chamber and a second chamber;
a storage vessel which stores a dialysate;
a dialysate exchange circuit which supplies the dialysate to the first chamber and discharges a waste dialysate in the second chamber to the outside by the consequent displacement of the partition wall to the second chamber side;
a dialysate supply circuit which supplies the dialysate in the first chamber to the dialyzer and discharges the waste dialysate from the dialyzer to the second chamber by the displacement of the partition wall to the first chamber side; and
a dialysate storage circuit which supplies the dialysate in the first chamber to the storage vessel by the displacement of the partition wall to the first chamber side,
the method comprising:
causing a control unit to implement a first control of supplying the dialysate to the first chamber of the vessel through the dialysate exchange circuit, displacing the partition wall of the vessel to the second chamber side, and discharging the waste dialysate in the second chamber of the vessel through the dialysate exchange circuit,
a second control of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side, and
a third control of supplying the dialysate in the first chamber to the dialyzer through the dialysate supply circuit and discharging the waste dialysate from the dialyzer to the second chamber through the dialysate supply circuit by the displacement of the partition wall to the first chamber side; and
causing the control unit to alternately implement at least either the second control or the third control, and the first control.

9. A water content removal system for removing water content from blood, comprising:
a separator through which blood passes and which separates the water content from the blood;
a vessel including a displaceable partition wall which partitions the inside of the vessel into a first chamber and a second chamber;
a storage vessel which stores a predetermined fluid;

a first circuit which supplies the fluid to the first chamber of the vessel;

a second circuit which discharges the water content in the second chamber of the vessel;

a third circuit which supplies the fluid in the first chamber of the vessel to the storage vessel; and a fourth circuit which discharges the water content from the separator to the second chamber, wherein the vessel is configured to be capable of displacing the partition wall to the first chamber side to push out the fluid from the first chamber and store the fluid in the storage vessel through the third circuit, and of discharging the water content from the separator to the second chamber through the fourth circuit by utilizing a negative pressure of the second chamber that has been generated by the displacement of the partition wall to the first chamber side, a control unit which implements a first control of supplying the fluid to the first chamber of the vessel through the first circuit, displacing the partition wall of the vessel to the second chamber side, and discharging the water content in the second chamber of the vessel through the second circuit, a second control of displacing the partition wall of the vessel to the first chamber side in a state where blood is being supplied to the separator so as to supply the fluid in the first chamber to the storage vessel through the third circuit, and discharging the water content from the separator to the second chamber through the fourth circuit by utilizing the negative pressure of the second chamber that has been generated by the displacement of the partition wall to the first chamber side, and a third control of supplying the fluid in the first chamber to the separator through the third circuit and discharging the water content from the separator to the second chamber by the displacement of the partition wall to the first chamber side, wherein the control unit alternately implements at least either the second control or the third control, and the first control.

10. The hemodialysis apparatus according to claim 3, further comprising:

a control unit which implements a first control of supplying the dialysate to the first chamber of the vessel through the dialysate exchange circuit, displacing the partition wall of the vessel to the second chamber side, and discharging the waste dialysate in the second chamber of the vessel through the dialysate exchange circuit, a second control of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side, and a third control of supplying the dialysate in the first chamber to the dialyzer through the dialysate supply circuit and discharging the waste dialysate from the dialyzer to the second chamber by the displacement of the partition wall to the first chamber side, wherein the control unit alternately implements at least either the second control or the third control, and the first control.

11. The hemodialysis apparatus according to claim 4, further comprising:

a control unit which implements a first control of supplying the dialysate to the first chamber of the vessel through the dialysate exchange circuit, displacing the partition wall of the vessel to the second chamber side, and discharging the waste dialysate in the second chamber of the vessel through the dialysate exchange circuit, a second control of displacing the partition wall of the vessel to the first chamber side in a state where blood is being supplied to the dialyzer so as to supply the dialysate in the first chamber to the storage vessel through the dialysate storage circuit, and discharging the water content of the blood from the dialyzer to the second chamber through the dialysate supply circuit by utilizing a negative pressure of the second chamber that has been generated by the displacement of the partition wall to the first chamber side, and a third control of supplying the dialysate in the first chamber to the dialyzer through the dialysate supply circuit and discharging the waste dialysate from the dialyzer to the second chamber by the displacement of the partition wall to the first chamber side, wherein the control unit alternately implements at least either the second control or the third control, and the first control.

12. The hemodialysis apparatus according to claim 6, wherein, in a valve for supplying and discharging the fluid to and from the vessel and the storage vessel, a portion that comes into contact with the fluid is formed on the cassette unit and a portion that does not come into contact with the fluid is formed on a body of the hemodialysis apparatus.

* * * * *